(12) United States Patent
Choi et al.

(10) Patent No.: US 11,987,582 B2
(45) Date of Patent: May 21, 2024

(54) MALEATE SALTS OF TRIAZOLOPYRAZINE DERIVATIVES, COMPOSITIONS, METHODS OF USE, AND PROCESSES OF MANUFACTURING THE SAME

(71) Applicant: ABION Inc, Seoul (KR)

(72) Inventors: Jun Young Choi, Seoul (KR); Kyung Eui Park, Seoul (KR); Yeong Mun Kim, Seoul (KR)

(73) Assignee: ABION Inc., Seoul (KR)

( * ) Notice: Subject to any disclaimer, the term of this patent is extended or adjusted under 35 U.S.C. 154(b) by 97 days.

(21) Appl. No.: 17/315,368

(22) Filed: May 10, 2021

(65) Prior Publication Data

US 2022/0235054 A1 Jul. 28, 2022

Related U.S. Application Data

(60) Provisional application No. 63/141,987, filed on Jan. 27, 2021.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .................................................. C07D 487/04
See application file for complete search history.

(56) References Cited

U.S. PATENT DOCUMENTS 9,403,831 B2 * 8/2016 Jung .................. A61K 31/4985

* cited by examiner

*Primary Examiner* — Shawquia Jackson

(57) ABSTRACT

Pharmaceutical compositions and methods of using maleate salts of triazolopyrazine derivatives are provided. In some aspects, the pharmaceutical compositions have improved storage stability and pharmacokinetic properties. The maleate salts of triazolopyrazine derivatives bind competitively to the phosphorylation site of c-MET kinase and can be used for the treatment or prevention of various hyperproliferative disorders.

38 Claims, 11 Drawing Sheets

FIG. 6

| Compound | Formulation/vehicle | pH Vehicle t=0 | pH t=(time) t=24h | pH t=(time) t=24h | Solubility (mg/mL) t=24h | XRPD t=24h |
|---|---|---|---|---|---|---|
| FB | PEG 400/PBS (50/50, w/v) | 7.3 | 8.2 | 8.2 | 0.27 | A |
| FB | PEG 400/DMSO/PBS (50/2/48, w/v/v) | 7.4 | 8.4 | 8.4 | 0.32 | A |
| FB | Transcutol/PBS (50/50, w/v) | 4.8 | 7.3 | 6.9 | 1.32 | A |
| FB | TPGS/PBS (20/80, w/v) | 7.2 | 7.8 | 7.7 | 1.84 | A |
| FB | Transcutol/PBS (10/90, w/v) | 6.7 | 7.6 | 7.5 | 0.05 | A |
| FB | TPGS/PBS (10/90, w/v) | 7.3 | 7.6 | 7.7 | 0.94 | A |
| Mae2 | PEG 400/PBS (50/50, w/v) | 7.3 | 6.9 | 3.7 | 1.5 | Am (wet) |
| Mae2 | PEG 400/DMSO/PBS (50/2/48, w/v/v) | 7.4 | 6.9 | 4.5 | 1.25 | Am (wet) |
| Mae2 | Transcutol/PBS (50/50, w/v) | 4.8 | 4.2 | 3.7 | >3.5 | - |
| Mae2 | TPGS/PBS (20/80, w/v) | 7.2 | 6.1 | 4.7 | 2.80 | A |
| Mae2 | Transcutol/PBS (10/90, w/v) | 6.7 | 5.3 | 4.8 | 0.35 | A |
| Mae2 | TPGS/PBS (10/90, w/v) | 7.3 | 5.3 | 5.0 | 1.47 | A |

MALEATE SALTS OF TRIAZOLOPYRAZINE DERIVATIVES, COMPOSITIONS, METHODS OF USE, AND PROCESSES OF MANUFACTURING THE SAME

CROSS-REFERENCE TO RELATED APPLICATIONS

This application claims priority from and the benefit of U.S. Provisional Application No. 63/141,987, filed on Jan. 27, 2021, which is hereby incorporated by reference for all purposes as if fully set forth herein

BACKGROUND

Triazolopyrazine derivatives have been described in U.S. Pat. No. 9,403,831 (which is incorporated by reference in its entirety herein) for use in inhibiting the activity of c-Met kinase, and for treatment hyperproliferative disorders. However, these triazolopyrazine derivatives are described in a free base form rather than a salt form.

What is needed are novel salt forms of novel triazolopyrazine derivatives having further advantageous properties while substantially retaining the pharmacokinetic and therapeutic effects of the free base form.

SUMMARY

Aspects described herein provide novel salt forms of triazolopyrazine derivatives represented by Chemical Formula 1 above with improved solubility, stability, and other properties while maintaining substantially similar pharmacokinetic properties of the free base form of the compounds.

In one aspect, maleate salts of triazolopyrazine derivatives represented by Chemical Formula 1(ABN 401) below are provided.

[Chemical Formula 1]

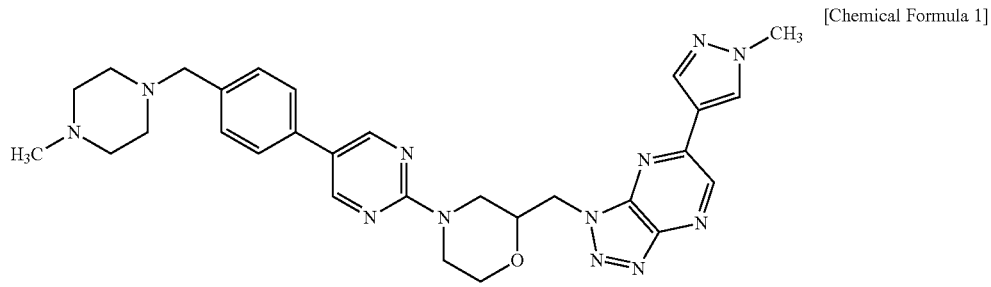

Aspects described herein provide a maleate salt of a triazolopyrazine derivative, represented by Chemical Formula 2:

[Chemical Formula 2]

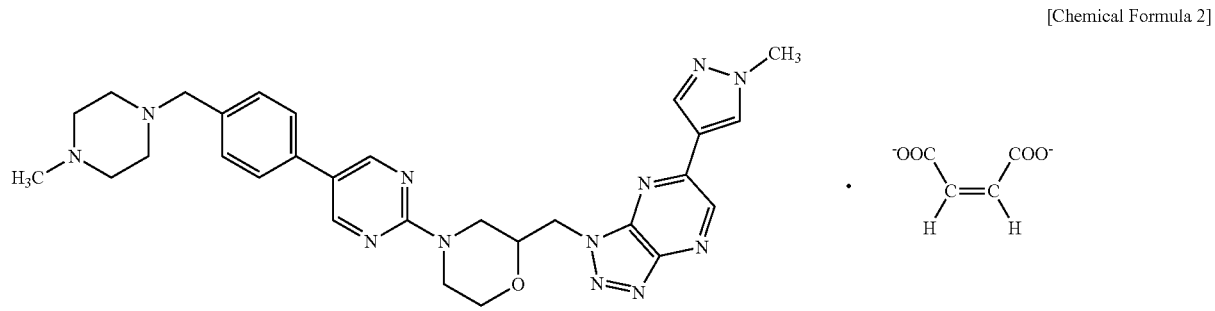

Further aspects provide methods for manufacturing a maleate salt of a triazolopyrazine derivative by (a) adding a compound represented by Chemical Formula 1 below to a reactor containing a solvent;

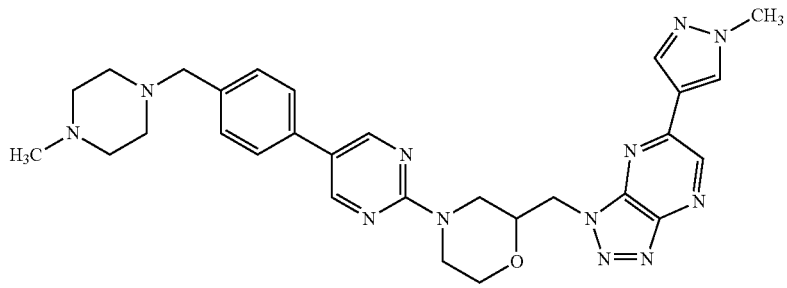

(b) stirring the compound and the solvent in the reactor; (c) adding maleic acid to the solution prepared in (b) in an equivalent ratio of about 1:1 to about 1:3 with respect to Chemical Formula 1; (d) stirring the maleic acid in the solution prepared in (c); and (e) cooling the solution prepared in (d) to obtain a precipitate of the maleate salt represented by Chemical Formula 2:

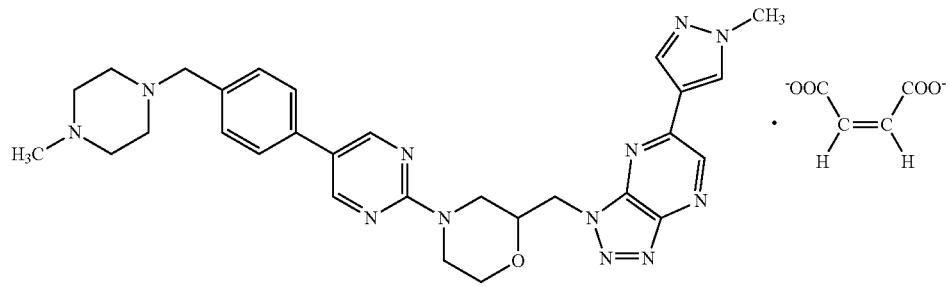

Further aspects provide a pharmaceutical composition comprising a maleate salt of a triazolopyrazine derivative, represented by Chemical Formula 2 below and a pharmaceutically acceptable salt.

[Chemical Formula 2]

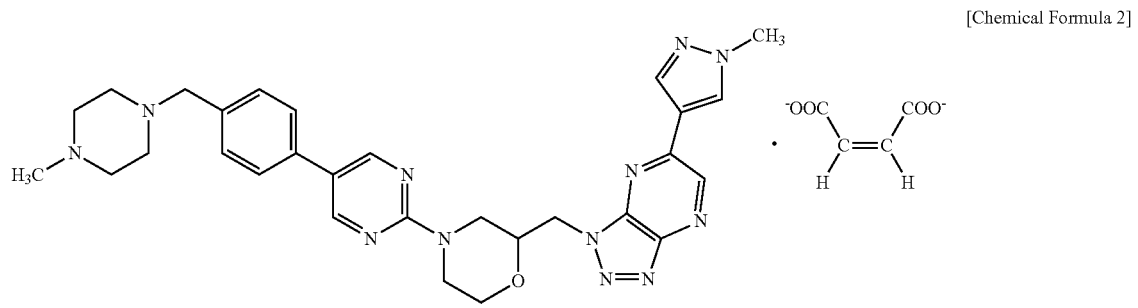

In yet another aspect, methods of inhibiting the activity of c-Met kinase in a subject are provided. This method comprises administering a maleate salt of a triazolopyrazine derivative, represented by Chemical Formula 2 to a subject in need of treatment for a disorder associated with an increased activity of c-Met kinase.

[Chemical Formula 2]

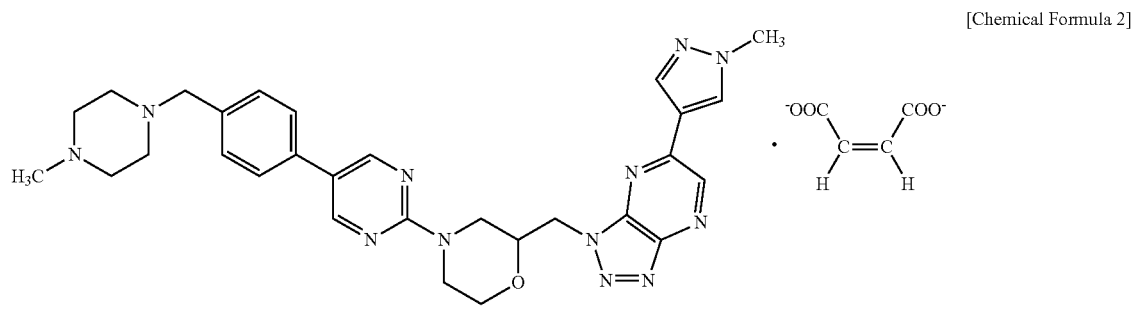

Aspects described herein improve the storage stability of a triazolopyrazine derivative ABN401 represented by Chemical Formula 1 by developing novel maleate salts of a compound of Chemical Formula 1.

An exemplary novel salt of the compound of Chemical Formula 1 above to be provided in the present disclosure include one or more maleate (maleic acid) counter ions (e.g., dimaleate).

Further, in the present disclosure, there is provided a manufacturing method of the salt and a pharmaceutical composition including the salt as active ingredients.

The present disclosure relates to novel salts of the triazolopyrazine derivative represented by Chemical Formula 1 above and a manufacturing method thereof, and the novels salt provided in the present disclosure improves the storage stability of the compound resulting in improved pharmaceutical usability and processability of the compound.

The novel salts of the compound inhibit the activity of c-Met tyrosine kinase, a kinase associated with various abnormal proliferative diseases associated with excessive cell proliferation and growth due to the abnormal activity of kinase, such as cancer, psoriasis, rheumatoid arthritis, and diabetic retinopathy. Further, the present disclosure describes exemplary pharmaceutical compositions for inhibiting the activity of c-Met tyrosine kinase including novel salts as active ingredients and a pharmaceutical composition for preventing or treating hyper proliferative disorders.

Aspects described herein provide pharmaceutical compositions comprising triazolopyrazine derivative maleate salts of the compound represented by Chemical Formula 1 below and a pharmaceutically acceptable excipient.

Aspects described herein provide methods of treating a hyperproliferative disorder with triazolopyrazine derivative maleate salts represented by Chemical Formula 1 below and a pharmaceutically acceptable excipient.

In one aspect, methods of treating a subject or patient are provided comprising administering one or more of the salt forms described herein to a subject or patient to treat, ameliorate, or prevent a hyperproliferative disease.

Further aspects provides methods of binding hepatocyte growth factor with a salt of the compound of Chemical Formula I by administering one or more of the salts described herein to a patient or subject.

BRIEF DESCRIPTION OF DRAWINGS

The above and other aspects, features and other advantages of the present aspects will be more clearly understood from the following detailed description taken in conjunction with the accompanying drawings, in which:

FIG. 6 shows the exemplary result of a solubility test of a maleate salt and free base of ABN 401.

DETAILED DESCRIPTION

Figure 1:
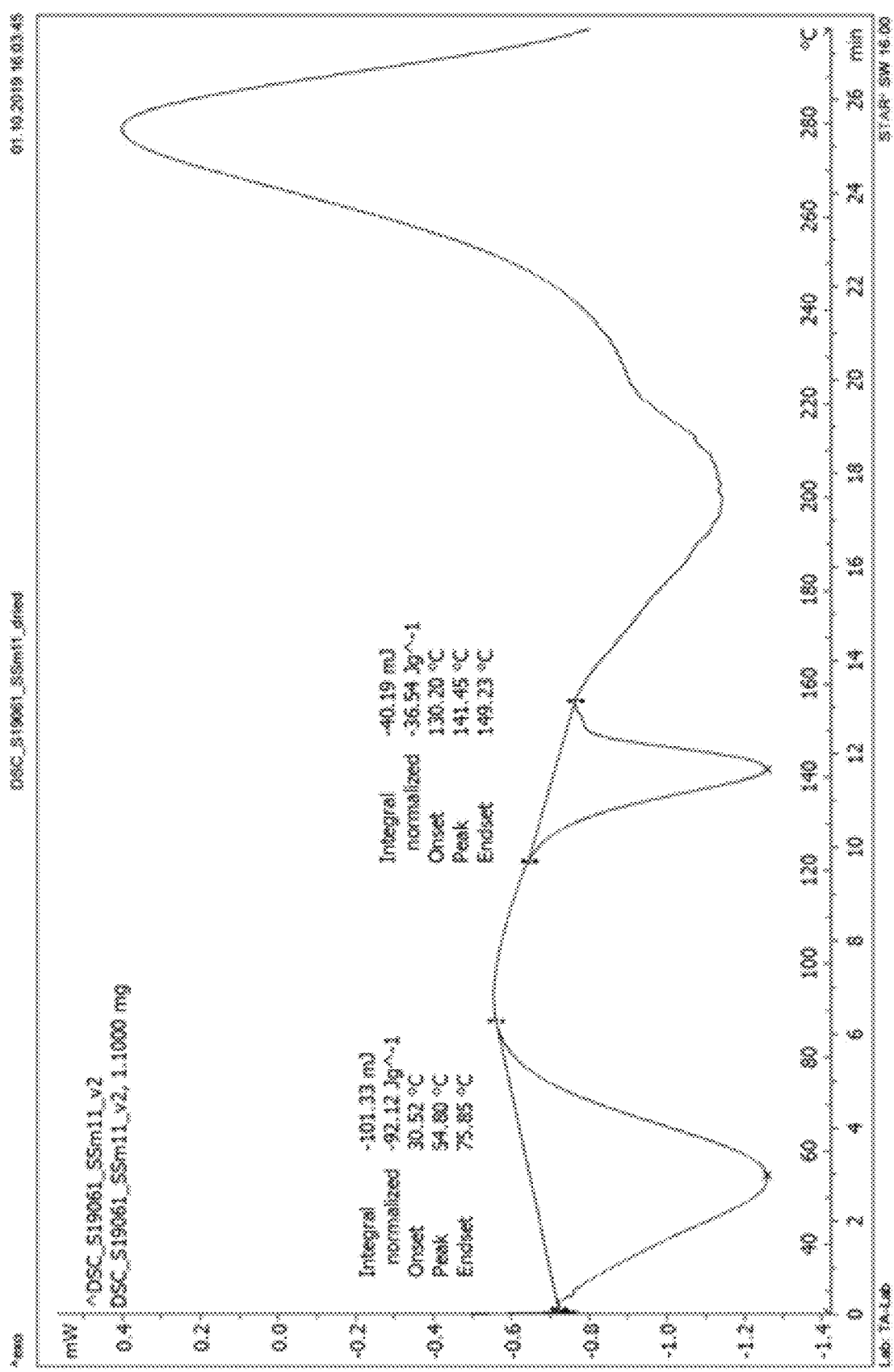
FIG. 1 shows an exemplary result of a DSC analysis of the maleate salt of Chemical Formula 1.

In some aspects, the present disclosure relates to novel maleate salts of a triazolopyrazine derivative represented by the following Chemical Formula 1, a manufacturing method thereof, and a pharmaceutical composition including the same. Surprisingly, the maleate salts described herein provide improved properties related to, for example, solubility and hygroscopicity, while substantially retaining the pharmacokinetic properties of the free base form.

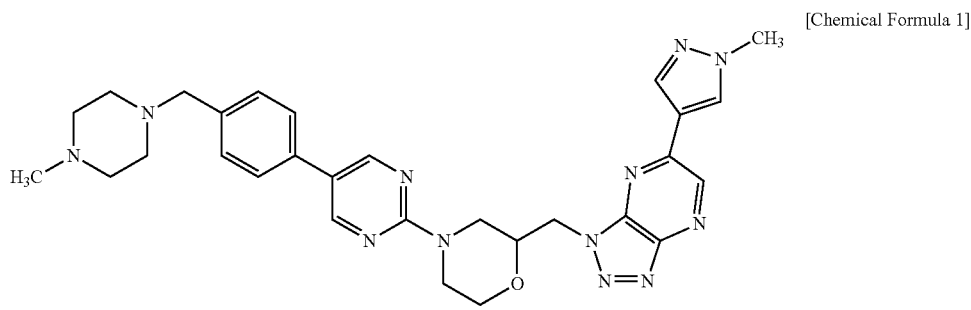

[Chemical Formula 1]

Aspects provided herein describe development of a composition for preventing or treating efficiently various hyper proliferative disorders caused by the abnormal activity of tyrosine kinase by finding the compound having the inhibitory activity on tyrosine kinase. As a result, the results described herein show that novel salts of the compound of Chemical Formula 1, which was not known until now, improved the storage stability of the compound while maintaining a function of inhibiting the activity of c-Met kinase of the compound.

Aspects described herein provide a maleate salt of a triazolopyrazine derivative, represented by Chemical Formula 2:

[Chemical Formula 2]

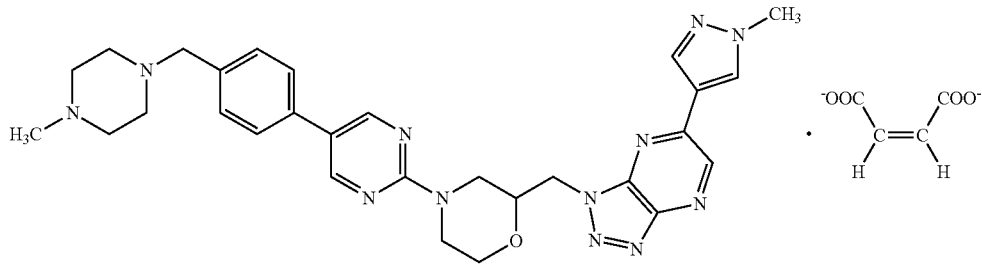

In some instances, the maleate salt has a chemical purity of at least about 4.7% greater than the free base form represented by Chemical Formula 1 after about 15 months at 40° C. and 75% relative humidity.

In some instances, the maleate salt has a water content of at least about 22% lower than the free base form represented by Chemical Formula 1 after about 15 months at 40° C. and 75% relative humidity.

In some instances, the maleate salt is more than 75% less soluble than the free base form represented by Chemical Formula 1 at a pH between 1 and 3.

In some instances, the maleate salt is more than 75% less soluble than the free base form represented by Chemical Formula 1 at a pH of about 1.2 in 0.05M gastric media.

In some instances, the salt form is characterized by a differential scanning calorimetry (DSC) thermogram with endothermic peaks at about 55° C. and about 145° C., and an exothermic peak at 280° C.

In some instances, the maleate salt has an H nuclear magnetic resonance spectrum (NMR) with peaks at 3.48-3.58 (m, 2H), 3.64 (br s, 3H), 3.87-4.03 (m, 4H), 4.17-4.28 (m, 1H,) 4.40 (br d, J=13.43 Hz, 1H), 4.74 (br d, J=12.21 Hz, 1H), 4.88-5.00 (m, 2H), 6.16 (s, 4H), 7.42 (d, J=8.24 Hz, 2H), 7.66 (d, J=8.24 Hz, 2H), 8.33 (d, J=0.61 Hz, 1H), 8.67 (s, 1H), 8.77 (s, 2H), and 9.23 (s, 1H)

Further aspects provide methods for manufacturing a maleate salt of a triazolopyrazine derivative by (a) adding a compound represented by Chemical Formula 1 below to a reactor containing a solvent;

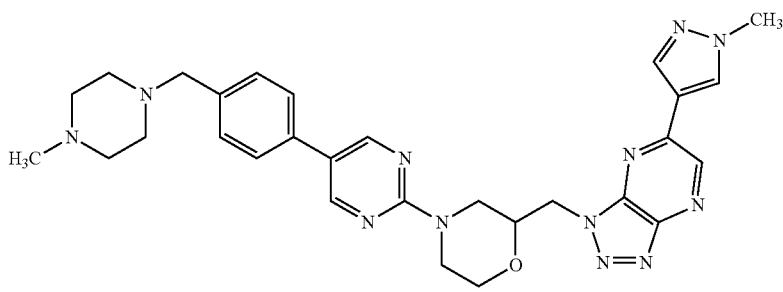

(b) stirring the compound and the solvent in the reactor to form a first solution; (c) adding maleic acid to the first solution in an equivalent ratio of about 1:1 to about 1:3 with respect to Chemical Formula 1 to form a second solution; (d) stirring the maleic acid in the second solution to form a third solution; and (e) cooling the third solution to obtain a precipitate of the maleate salt represented by Chemical Formula 2:

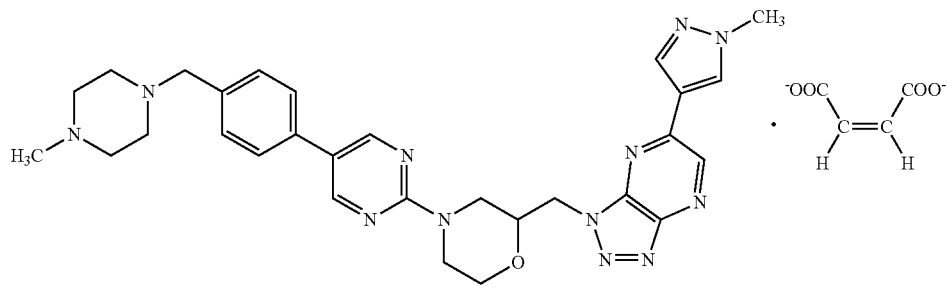

In some instances, the maleate salt comprises at least one maleic acid molecule.

In some instances, the maleate salt comprises at least two maleic acid molecules.

In some instances, the solvent is selected from the group consisting of acetonitrile, acetone, and 1,2-dimethoxyethane.

In some instances, step (b) is performed at about 50° C. for at least about 1 hour.

In some instances, the precipitate is cooled to about 25° C. and then aged for at least about 24 to 48 hours.

Further aspects provide a pharmaceutical composition comprising a maleate salt of a triazolopyrazine derivative, represented by Chemical Formula 2 below and a pharmaceutically acceptable carrier In some instances, the disorder is a hyperproliferative disorder.

In some instances, the hyperproliferative disorder is selected from the group consisting of lung cancer, gastric cancer, pancreatic cancer, colon cancer, ovarian cancer, renal cell cancer, prostate cancer and a brain tumor.

In some instances, the maleate salt is administered in a therapeutically effective amount to the subject.

According to aspects described herein, the novel salts described herein bind competitively to phosphorylation site of c-MET kinase, thereby significantly inhibiting the activity of c-MET kinase that triggers proliferation and migration of cells and formation of new blood vessels.

Therefore, the salts described may be usefully used for treating or preventing various hyper proliferative disorders mediated by hyper proliferation activation of cells and excessive angiogenesis.

[Chemical Formula 2]

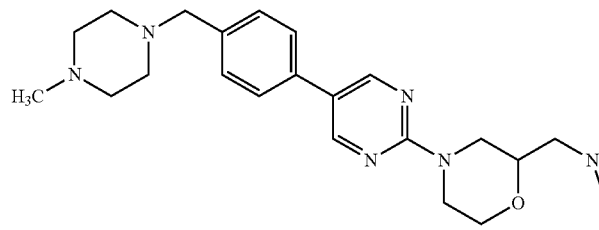
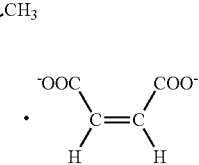

In some instances, the pharmaceutically acceptable carrier is selected from the group consisting of one or more of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil.

In some instances, the pharmaceutical composition further comprises one or more of a lubricant, a wetting agent, a sweetening agent, a flavoring agent, an emulsifying agent, a suspending agent, and a preservative.

In yet another aspect, methods of inhibiting the activity of c-Met kinase in a subject are provided. This method comprises administering a maleate salt of a triazolopyrazine derivative, represented by Chemical Formula 2 to a subject in need of treatment for a disorder associated with an increased activity of c-Met kinase.

The novel salts described herein exhibit physical properties, for example, melting point, hygroscopicity, solubility, fluidity, or thermal stability, which are surprisingly different from those of a pure compound while substantially retaining the pharmacokinetic properties of the free base form.

The term "substantially retaining the pharmacokinetic properties," as used herein, refers to a salt form having at least 50, 60, 70, 80, 90, or 100% of the various pharmacokinetic parameters of the free base form as described herein.

Figure 7:
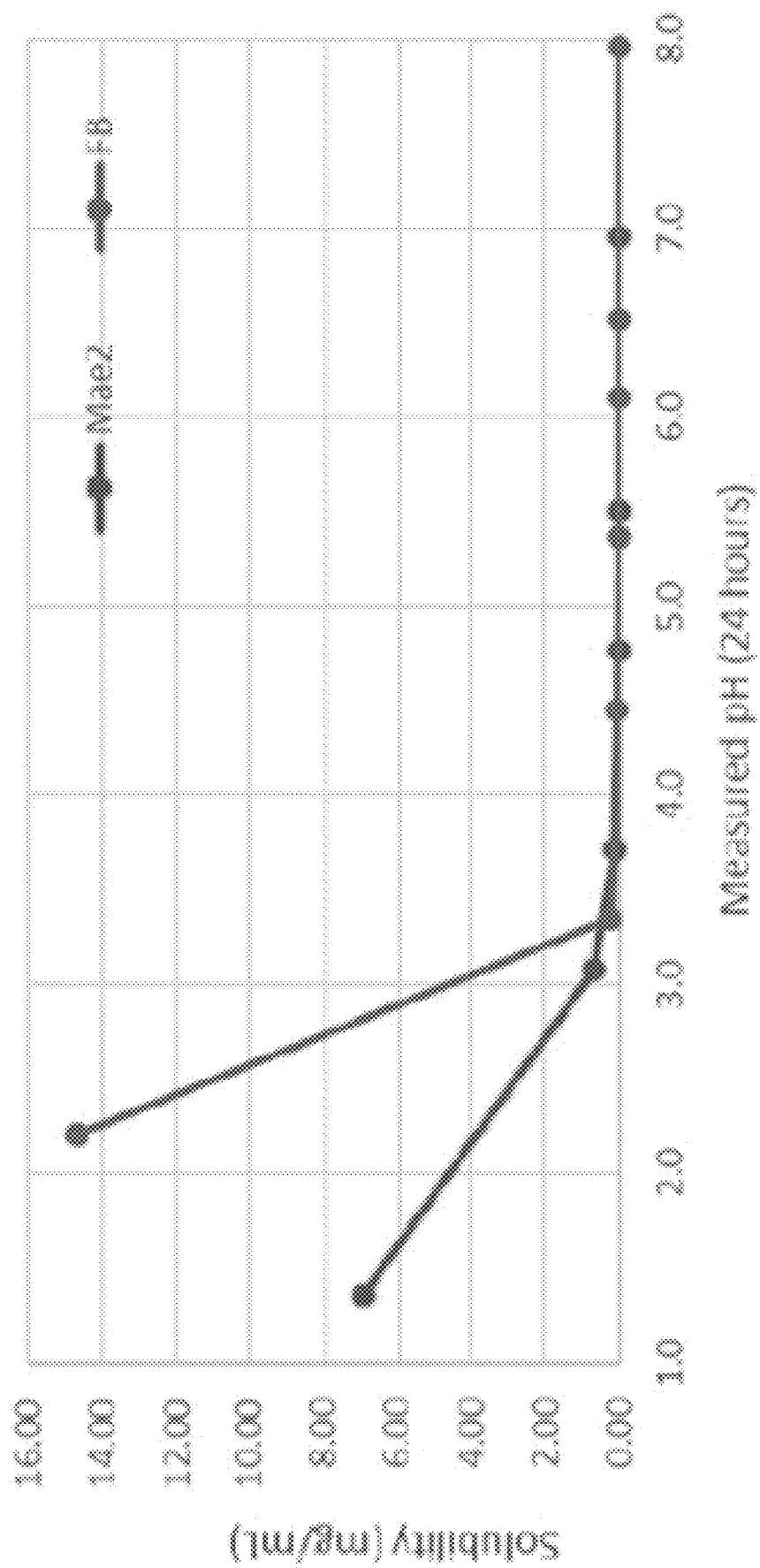
FIG. 7 shows an exemplary comparison of the solubility of a maleate salt and a free base of ABN 401 at different pHs.

In one aspect, as shown herein and in, the maleate salts (e.g., maleate salt, dimaleate salt) described herein surprisingly exhibit decreased solubility compared to the free base (non-salt) form of the compound. For example, as shown in FIG. 7, the maleate salt (Chemical Formula 2) is more than 50% less soluble at gastric pH).

[Chemical Formula 2]

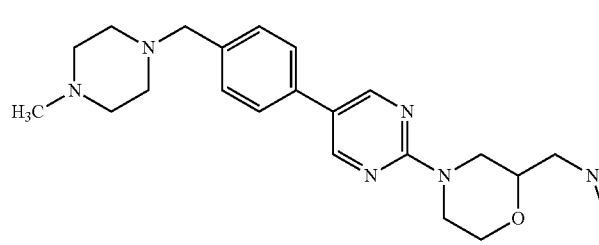
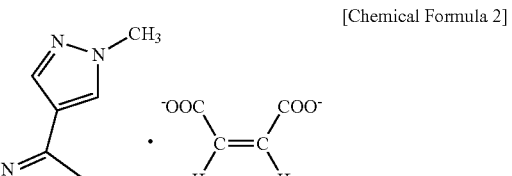

TABLE 1

Buffer solutions that were used in
the pH-dependent solubility study

| pH | Composition buffer solution |
|---|---|
| 1.2 | 0.05M Gastric buffer |
| 3 | 0.05M Citrate buffer |
| 4 | 0.05M Citrate buffer |
| 5 | 0.05M Citrate buffer |
| 6 | 0.05M and 0.2M Phosphate buffer |
| 7.4 | 0.05M Phosphate buffer |

Ordinarily, a salt form of a compound would be expected to have increased solubility rather than decreased solubility compared to a free base form. See, e.g., *Handbook of Pharmaceutical Salts: Properties, Selection, and Use*, Edited by P. Heinrich Stahl and Camile G. Wermuth. VHCA, Verlag Helvetica Chimica Acta, Zürich, Switzerland, and Wiley-VCH, Weinheim, Germany. Introduction, Page 2, Paragraph 2, 2002.

Figure 4:
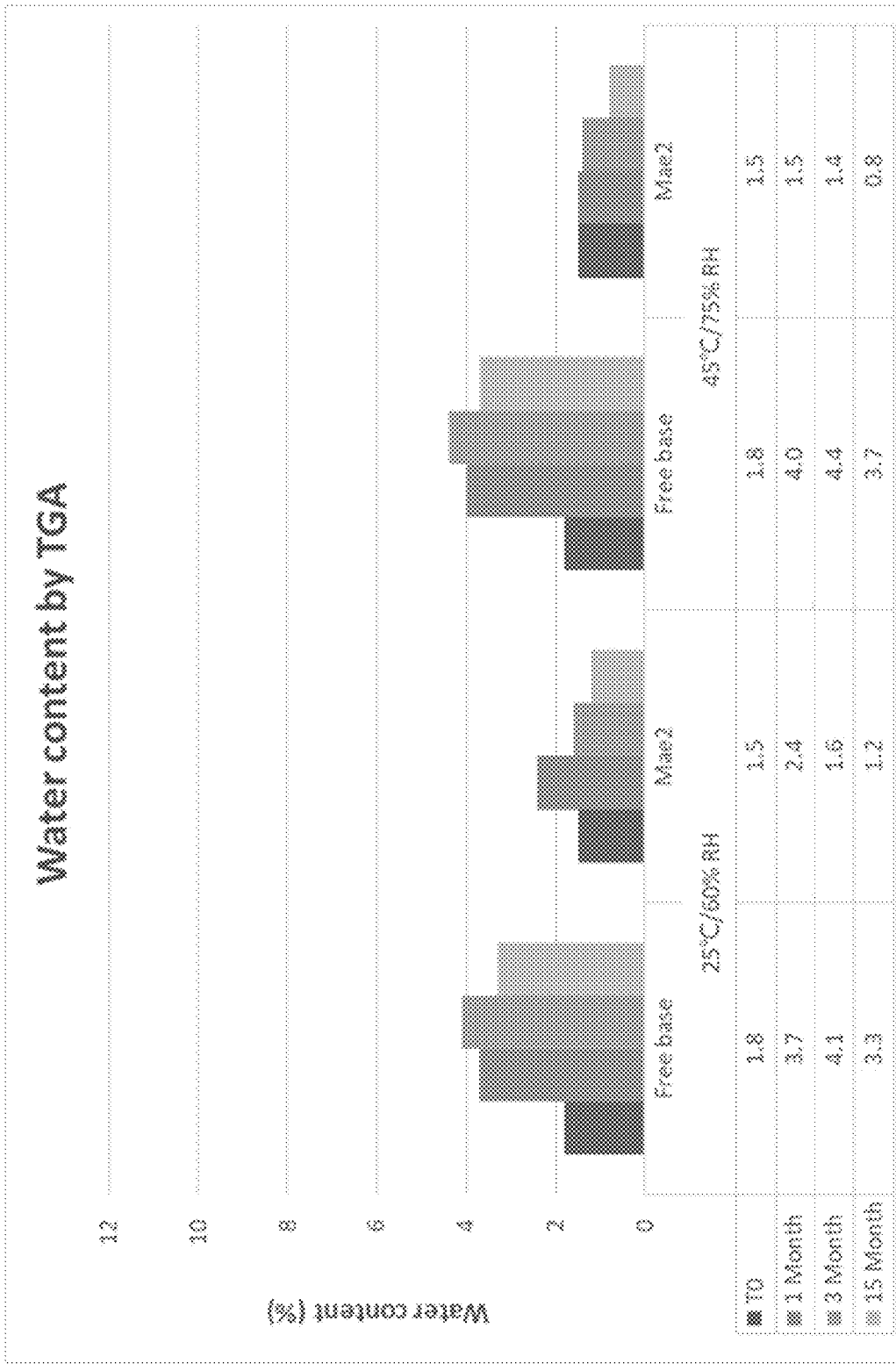
FIG. 4 shows a result of an exemplary test of water uptake by TGA in the maleate salt described herein.

The maleate salts described herein exhibit surprisingly reduced solubility and hygroscopicity. As shown in FIG. 4, the maleate salt (Mae2) shows significantly lower water content at 40 degrees centigrade, and 75% relative humidity (right panel) compared to the free base form over time (nearly four times lower at 15 months).

The maleate salts described herein exhibit greater stability compared to the free base form of the compound. As shown in the exemplary experiment illustrated in FIG. 5, the maleate salt of Compound I generally have greater chemical purity over time at 40 degrees centigrade and 75% relative humidity (right panel) compared to the free base form. In particular, the maleate salt form exhibits at least about 4.7% greater chemical purity at 15 months.

Figure 8:
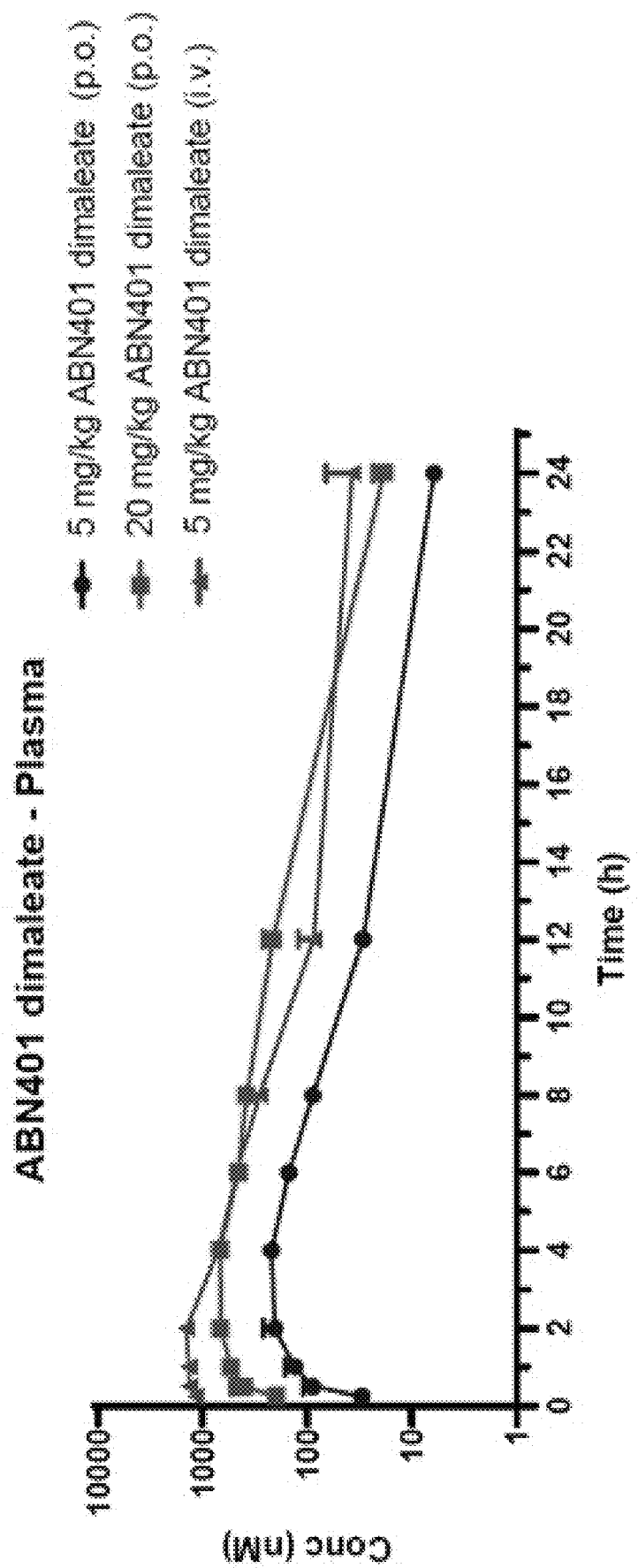
FIG. 8 shows exemplary pharmacokinetic properties of a dimaleate salt.
Figure 9:
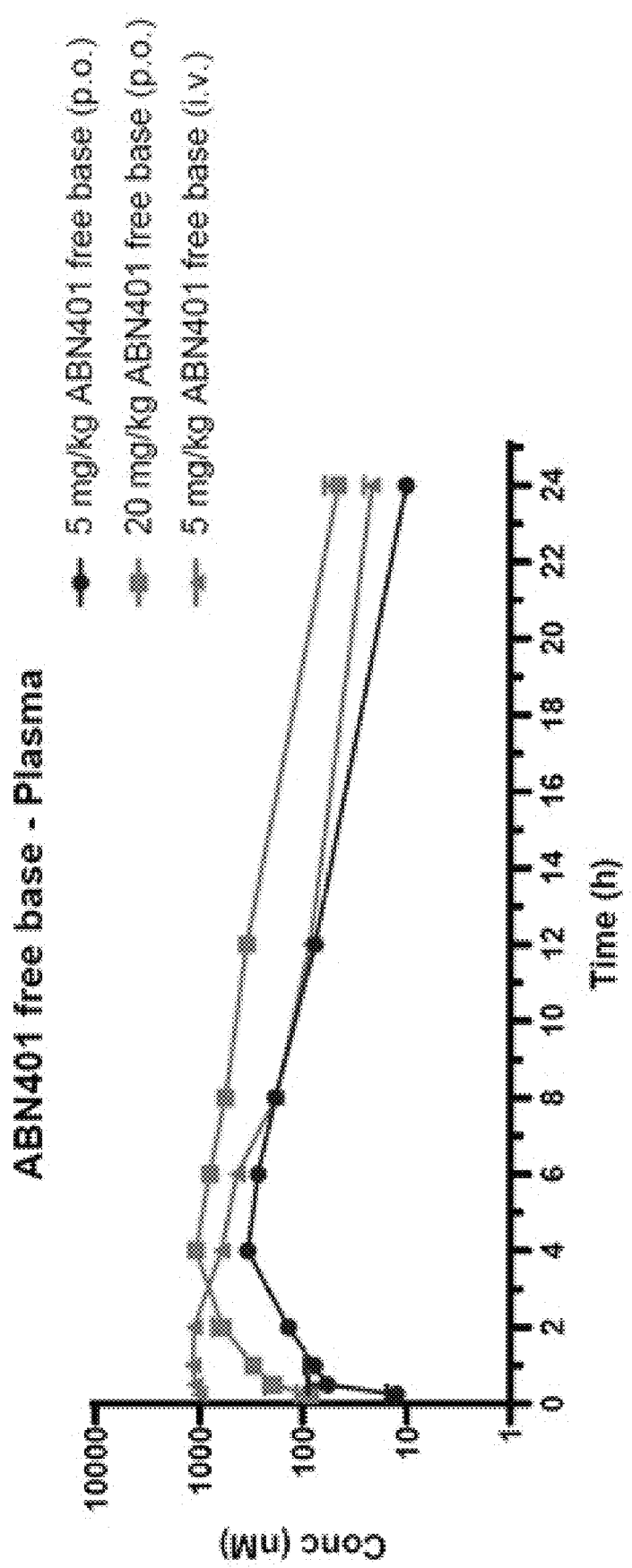
FIG. 9 shows exemplary pharmacokinetic properties of a free base of ABN 401.

In addition, to increased stability, lower solubility and lower hygroscopicity, the maleate salts described herein maintain substantially similar PK properties (see, e.g., FIGS. 8 and 9).

FIG. 8 shows the concentration of the dimaleate salt form of the compound of Chemical Formula 2 in plasma over time at the indicated concentrations in Wistar rats after a single administration. The pharmacokinetic (PK) properties are shown in Table 2 below.

TABLE 2

PK parameters of the Compound of Chemical Formula 2 Single Administration

| | | Dose Level (mg/kg) | | | | | |
|---|---|---|---|---|---|---|---|
| | | 5 | | 5 | | 20 | |
| | | | | Route | | | |
| | | IV | | PO | | PO | |
| | | Mean | SD | Mean | SD | Mean | SD |
| $T_{max}$ | (h) | | | 2-4$ | n/a | 2-4$ | n/a |
| $C_{max}$ | (nM) | | | 246 | 65.2 | 676 | 15.5 |
| $AUCl_{ast}$ | (h*nM) | 8130 | 441 | 1730 | 117 | 6820 | 836 |
| $AUC_{last}$/Dose | (h*kg*nM/mg) | 1630 | 88.2 | 347 | 23.4 | 341 | 41.8 |
| $AUC\infty$ | (h*nM) | 8265 | n/a | 1770 | 101 | 6930 | 769 |
| $AUC\infty$/Dose | (h*kg*nM/mg) | 1655 | n/a | 355 | 20.1 | 346 | 38.5 |
| Vz | (mg/(nM)/kg) | 0.00259 | n/a | | | | |
| Cl | (mg/(h*nM)/kg) | 0.000606 | n/a | | | | |
| Vss | (mg/(nM)/kg) | 0.00271 | n/a | | | | |
| F | (%) | | | 21.4 | | 20.9 | | n/a: not applicable
$range

FIG. 9 shows the concentration of the free base form of the compound of Formula 1 in plasma over time at the indicated concentrations in Wistar rats after a single administration. The pharmacokinetic (PK) properties are shown in Table 3 below.

TABLE 3

PK parameters Chemical Formula 1 single administration

| | | Dose Level (mg/kg) | | | | | |
|---|---|---|---|---|---|---|---|
| | | 5 | | 5 | | 20 | |
| | | | | Route | | | |
| | | IV | | PO | | PO | |
| | | Mean | SD | Mean | SD | Mean | SD |
| $T_{max}$ | (h) | | | 4 | n/a | 4 | n/a |
| $C_{max}$ | (nM) | | | 343 | 13.2 | 1080 | 116 |

TABLE 3-continued

PK parameters Chemical Formula 1 single administration

| | | Dose Level (mg/kg) | | | | | |
|---|---|---|---|---|---|---|---|
| | | 5 | | 5 | | 20 | |
| | | Route | | | | | |
| | | IV | | PO | | PO | |
| | | Mean | SD | Mean | SD | Mean | SD |
| $AUC_{last}$ | (h*nM) | 7060 | 1030 | 2750 | 192 | 9760 | 898 |
| $AUC_{last}$/Dose | (h*kg*nM/mg) | 1410 | 207 | 551 | 38.4 | 488 | 44.9 |
| $AUC\infty$ | (h*nM) | 7200 | 1070 | 2810 | 192 | 10100 | 623 |
| $AUC\infty$/Dose | (h*kg*nM/mg) | 1440 | 214 | 562 | 38.4 | 504 | 31.1 |
| Vz | (mg/(nM)/kg) | 0.00471 | 0.00102 | | | | |
| Cl | (mg/(h*nM)/kg) | 0.000705 | 0.000104 | | | | |
| Vss | (mg/(nM)/kg) | 0.00347 | 0.000359 | | | | |
| F | (%) | | | 39.0 | | 35.0 | | n/a: not applicable

As shown in FIGS. 8 and 9 and Tables 2 and 3, the PK properties of the free base and dimaleate forms of the compound of Formula 1 are substantially similar.

Figure 10:
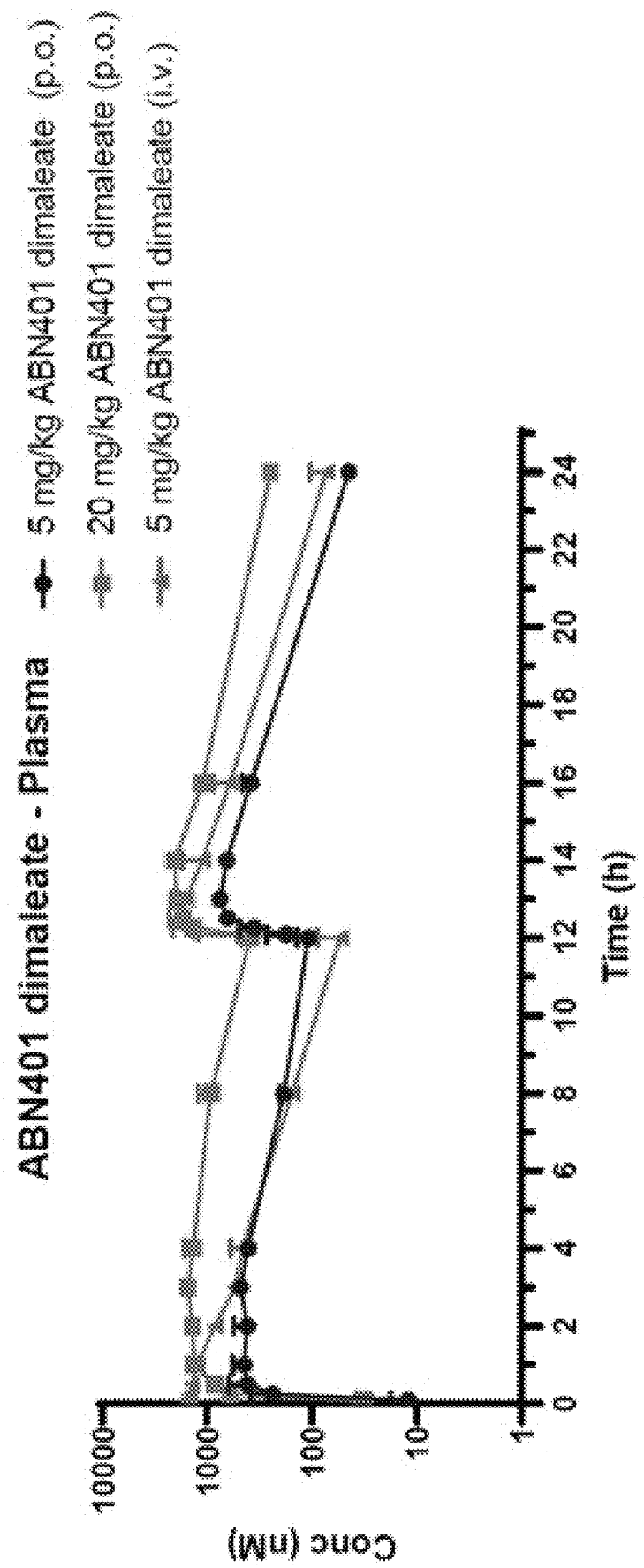
FIG. 10 shows pharmacokinetic properties of a dimaleate salt bid (twice a day)

FIG. 10 and Table 4 show the PK properties of the compound of Chemical Formula 2 administered twice a day (bid).

TABLE 4

PK parameters of the Compound of Chemical Formula 2 bid Administration

Figure 11:
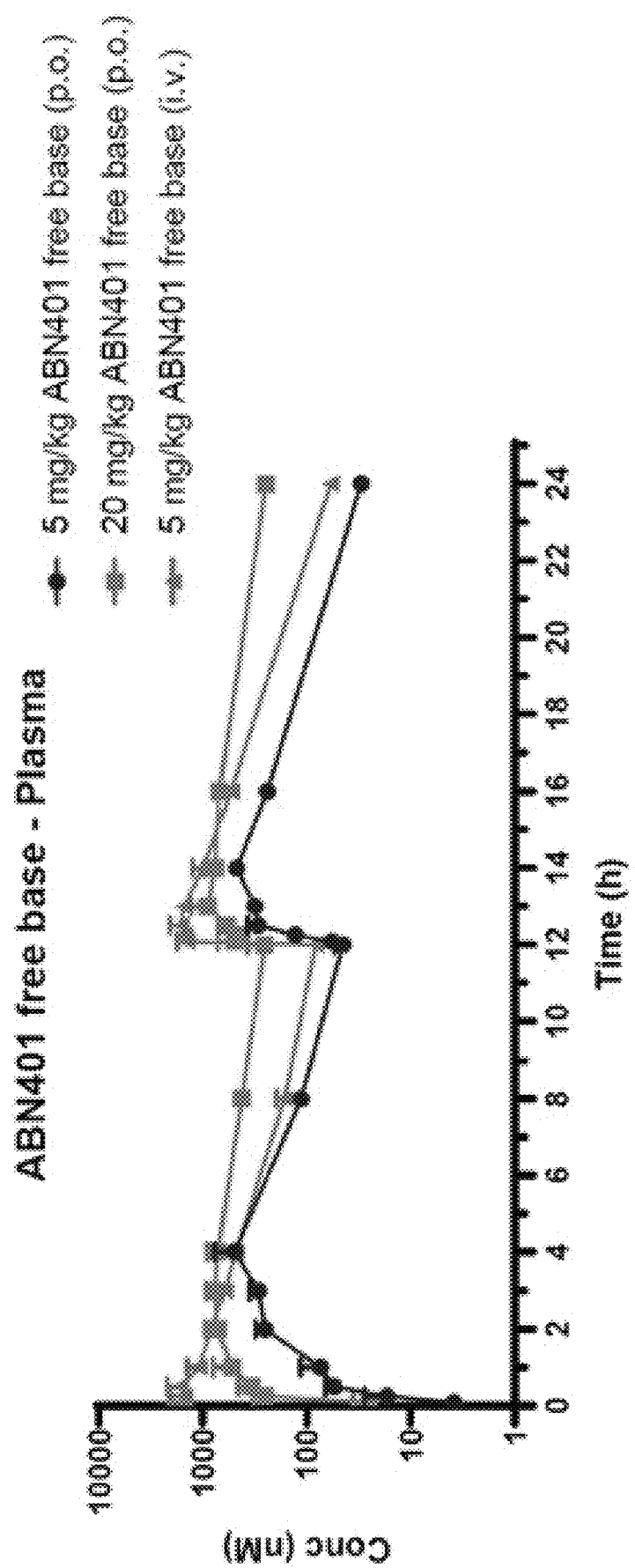
FIG. 11 shows exemplary pharmacokinetic properties of a free base of ABN 401.

| | | Dose Level (mg/kg) | | | | | |
|---|---|---|---|---|---|---|---|
| | | 5 | | 5 | | 20 | |
| | | Total Daily Dose Level (mg/kg/day) | | | | | |
| | | 10 | | 10 | | 40 | |
| | | Route | | | | | |
| | | IV | | PO | | PO | |
| | | Mean | SD | Mean | SD | Mean | SD |
| $T_{max1}$ | (h) | | | 0.5-3$ | n/a | 2-3$ | n/a |
| $T_{max2}$ | (h) | | | 12.5-13$ | n/a | 12.5-14$ | n/a |
| $C_{max1}$ | (nM) | | | 611 | 195 | 1600 | 421 |
| $C_{max2}$ | (nM) | | | 802 | 216 | 2120 | 553 |
| $AUC_{(0-12\ h)}$ | (h*nM) | 5320 | 1310 | 3430 | 487 | 12200 | 4560 |
| $AUC_{(0-12\ h)}$/Dose | (h*kg*nM/mg) | 1060 | 262 | 685 | 97.4 | 612 | 228 |
| $AUC_{(12-24\ h)}$ | (h*nM) | 7340 | n/a | 3990 | 852 | 12000 | 1030 |
| $AUC_{(12-4\ h)}$/Dose | (h*kg*nM/mg) | 1470 | n/a | 798 | 170 | 601 | 51.6 |
| $AUC_{last}$ | (h*nM) | 12975 | n/a | 7420 | 1340 | 24300 | 5550 |
| $AUC_{last}$/Dose | (h*kg*nM/mg) | 1298 | n/a | 742 | 134 | 607 | 139 |
| Vz | (mg/(nM)/kg) | 0.00283 | n/a | | | n/a | n/a |
| Cl | (mg/(h*nM)/kg) | 0.000860 | n/a | | | n/a | n/a |
| Vss | (mg/(nM)/kg) | 0.00782 | n/a | | | n/a | n/a |
| F | (%) | | | 57.2 | | 46.8 | | tmax1 and cmax1, tmax2 and cmax2 were after the first and second daily dosing, respectively
n/a: not applicable
$range FIG. 11 and Table 5 show the PK properties of the compound of Chemical Formula 1 administered twice per day.

TABLE 5

PK parameters of the Compound of Chemical Formula 1 bid Administration

| | | Dose Level (mg/kg) | | | | | |
|---|---|---|---|---|---|---|---|
| | | 5 | | 5 | | 20 | |
| | | Total Daily Dose Level (mg/kg/day) | | | | | |
| | | 10 | | 10 | | 40 | |
| | | Route | | | | | |
| | | IV | | PO | | PO | |
| | | Mean | SD | Mean | SD | Mean | SD |
| $T_{max1}$ | (h) | | | 3-4$ | n/a | 1-3$ | n/a |
| $T_{max2}$ | (h) | | | 13-14$ | n/a | 12.083-16$ | n/a |
| $C_{max1}$ | (nM) | | | 564 | 425 | 821 | 396 |
| $C_{max2}$ | (nM) | | | 488 | 114 | 1000 | 472 |
| $AUC_{(0-12\ h)}$ | (h*nM) | 5360 | 2320 | 2440 | 1160 | 7900 | n/a |
| $AUC_{(0-12\ h)}$/Dose | (h*kg* nM/mg) | 1070 | 465 | 487 | 232 | 395 | n/a |
| $AUC_{(12-24\ h)}$ | (h*nM) | 7380 | 1980 | 2450 | 421 | 6260 | 1970 |
| $AUC_{(12-4\ h)}$/Dose | (h*kg*nM/mg) | 1480 | 395 | 490 | 84.3 | 313 | 98.4 |
| $AUC_{last}$ | (h*nM) | 14100 | 3460 | 4880 | 1320 | 12700 | 3410 |
| $AUC_{last}$/Dose | (h*kg*nM/mg) | 1410 | 346 | 488 | 132 | 318 | 85.2 |
| Vz | (mg/(nM)/kg) | 0.00265 | 0.00102 | | | | |
| Cl | (mg/(h*nM)/kg) | 0.000733 | 0.000193 | | | | |
| Vss | (mg/(nM)/kg) | 0.00760 | 0.00283 | | | | |
| F | (%) | | | 34.6 | | 22.6 | | tmax1 and cmax1, tmax2 and cmax2 were after the first and second daily dosing, respectively
n/a: not applicable
$range As shown in FIGS. 10 and 11 and Tables 4 and 5, the PK properties of the free base and dimaleate forms of the compound of Formula 1 are substantially similar.

Accordingly, the salts described herein may be used for selecting the most suitable form for pharmacological use in a manufacturing process of drugs, a manufacturing process of separate drug formulations such as tablets, capsules, ointments, and suspensions, or manufacturing of a drug form having optimal pharmacokinetic properties.

In one aspect, methods of treating a subject or patient are provided comprising administering one or more of the salt forms described herein to a subject or patient to treat, ameliorate, or prevent a hyperproliferative disease.

Further aspects provide methods of binding hepatocyte growth factor by administering one or more of the salts described herein to a patient or subject.

According to another aspect of the present disclosure, a pharmaceutical composition is provided, including a therapeutically effective amount of novel salts of Chemical Formula 1 above. For example, the present disclosure provides a pharmaceutical composition for prevention or treatment of hyper proliferative disorders, including the novel salts of the compound of Chemical Formula 1 described above as active ingredients.

In this specification, the term "hyper proliferative disorder" refers to a pathological condition caused by excessive growth, division, and migration of cells that are not normally regulated by a general restriction means in an animal body which is normally growing. Examples of the hyper proliferative disorders prevented or treated with the composition of the present disclosure include cancer, diabetic retinopathy, retinopathy of prematurity, corneal transplant rejection, neovascular glaucoma, hypoxia, proliferative retinopathy, psoriasis, rheumatoid arthritis, osteoarthritis, autoimmune disease, Crohn's disease, recurrent stenosis, atherosclerosis, intestinal adhesions, ulcers, hepatopathy, glomerulonephritis, diabetic nephropathy, malignant neuropathy, thrombotic microangiopathy, organ graft rejection, and glomerulopathy, but are not limited thereto and include all hyper proliferative disorders which are caused by abnormal proliferation of cells and overgrowth of new blood vessels.

More preferably, the cancer, which is one of the hyper proliferative disorders to be prevented and treated with the composition of the present disclosure, includes lung cancer, gastric cancer, pancreatic cancer, colon cancer, ovarian cancer, renal cell cancer, prostate cancer or brain tumor.

The term "therapeutically effective amount" refers an amount of an active pharmaceutical ingredient sufficient to treat, ameliorate, cure, or reduce symptoms of a disease or condition.

When the composition of the present disclosure is manufactured as a pharmaceutical composition, the pharmaceutical composition of the present disclosure includes a pharmaceutically acceptable carrier. The pharmaceutically acceptable carrier to be included in the pharmaceutical composition of the present disclosure is generally used in preparation and includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil, but is not limited thereto. The pharmaceutical composition of the present disclosure may further include a lubricant, a wetting agent, a sweetening agent, a flavoring agent, an emulsifying agent, a suspending agent, a preservative, and the like, in addition to the ingredients. The pharmaceutical composition can be provided is any suitable dosage form (e.g., oral solution, emulsion, syrup, elixir, tablet, capsule, liquid-filled capsule, softgel, extended-release and solid dosage form, etc.).

In one aspect, although the compound of Chemical Formula I can successfully be manufactured as a general pharmaceutical compositions, the physical properties such as solubility and thermal stability of the compound of Chemical Formula 2 may have certain advantages for manufacturing a general pharmaceutical composition.

Accordingly, the present inventors have performed various salt screenings to develop salts suitable for manufacturing a pharmaceutical formulation such as improving the solubility and stability of the triazolopyrazine derivative, and as a result, have developed novel salts having high solubility and excellent stability while the pharmacological activity of the compound was constantly maintained.

Hereinafter, the present disclosure will be described in more detail through examples of the present disclosure, but the scope of the present disclosure is not limited by the following examples.

The present disclosure relates to novel maleate salts of a compound of Chemical Formula 1 capable of effectively preventing or treating various hyper proliferative disorders by inhibiting the activity of c-Met kinase and a manufacturing method thereof.

The present disclosure relates to novel maleate salts of the compound represented by Chemical Formula 1 above, and hereinafter, a method of manufacturing salts of the compound of Chemical Formula 1 above will be described.

Hereinafter, examples to be described below may be modified into various other forms, and the scope of the present disclosure is not limited to examples to be described below. Examples of the present disclosure are provided to those skilled in the art for more completely describing the present disclosure.

An example of a maleate salt of the triazolopyrazine derivative to be provided in the present disclosure is represented by the following Chemical Formula 2.

Example 1: Manufacture of the Maleate Salt of ABN401

300 mg of a Chemical Formula 1 was dissolved in 5 mL of acetonitrile, 130 mg of maleic acid was added to the solution so that a molar ratio of the compound of Chemical Formula 1 and the maleic acid was 1:2.1. 5 ml of the maleic acid solution at a concentration of 20 mg/ml was added and the reaction was performed at 50° C. for 1 hour.

The reaction solution was cooled to 25° C. at an interval of 5° C., and then aged for 48 hours to obtain 350 mg of crystals of the compound of Chemical Formula 2.

The crystals were washed with distilled water and dried in a vacuum state of 10 mbar and 50° C.

An H nuclear magnetic resonance spectrum (NMR) was confirmed to identify the compound of Chemical Formula 2 obtained through the step and the peaks are listed below.

1H NMR (500 MHz, DMSO-d6) δ ppm 2.78 (br s, 3H) 3.48-3.58 (m, 2H) 3.64 (br s, 3H) 3.87-4.03 (m, 4H) 4.17-4.28 (m, 1H) 4.40 (br d, J=13.43 Hz, 1H) 4.74 (br d, J=12.21 Hz, 1H) 4.88-5.00 (m, 2H) 6.16 (s, 4H) 7.42 (d, J=8.24 Hz, 2H) 7.66 (d, J=8.24 Hz, 2H) 8.33 (d, J=0.61 Hz, 1H) 8.67 (s, 1H) 8.77 (s, 2H) 9.23 (s, 1H)

The DSC analysis result regarding the maleate salt shows that the maleate is endothermic at 25° C. to 100° C. Without being bound by theory, it is believed that this result is associated with evaporation of water. In addition, the DSC results show a strong endothermic peak at 145.1° C., indi-

[Chemical Formula 2]

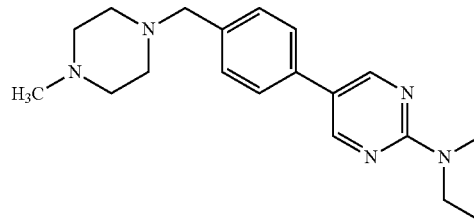 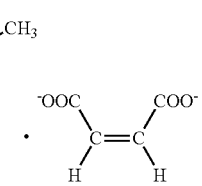

The exemplary maleate salt may be formed by binding at least one maleic acid molecule to the triazolopyrazine derivative of the compound of Chemical Formula 1. In one aspect, the maleate comprises two maleic acid molecules (dimaleate).

Differential scanning calorimetry (DSC) analysis was performed to confirm the thermal stability of the novel salts provided in the present disclosure, and dynamic vapor sorption (DVS) analysis was performed to confirm the hygroscopicity.

The DSC analysis was performed to confirm the thermal fluidity of the salts by using a DSC3+ STARe device, and samples of the salts were mounted on an aluminum fan, and then heated to 25° C. to 300° C. using a pinhole, and a heating rate of 10° C./MIN was applied.

The DVS analysis was performed to confirm the hygroscopicity of the salts by using a DVS-1 device, and was performed at a relative humidity of 40%, 95%, and 0% at 25° C. for 60 minutes.

cating the melting of the maleate salt and an improved thermal stability compared to the pure material.

The DSC analysis result shows that the salt form is characterized with endothermic peaks at about 55° C. and about 145° C., and an exothermic peak at 280° C.

Figure 2:
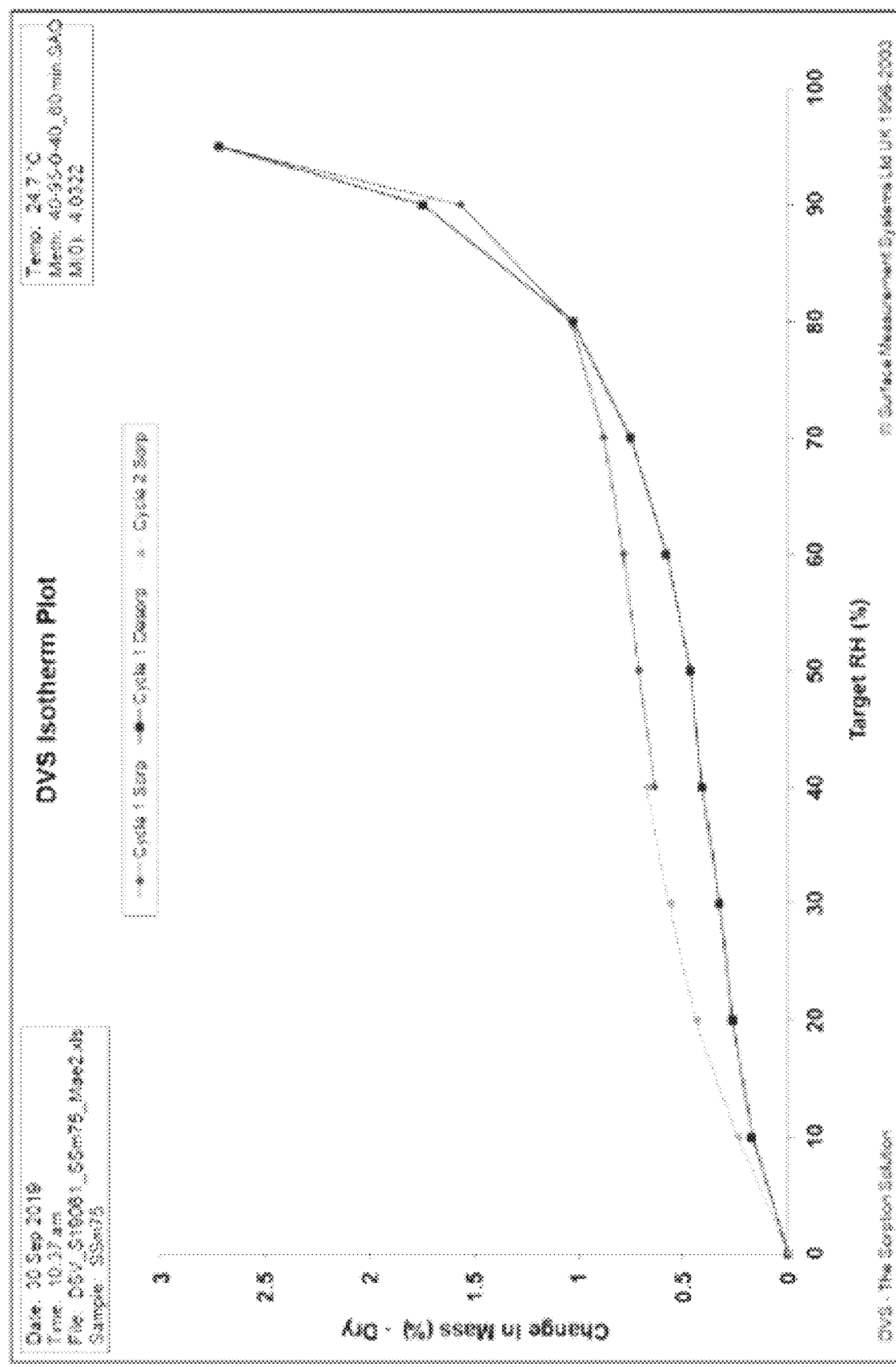
FIG. 2 shows an exemplary result of a DVS analysis of the maleate salt of Chemical Formula 1.
Figure 3:
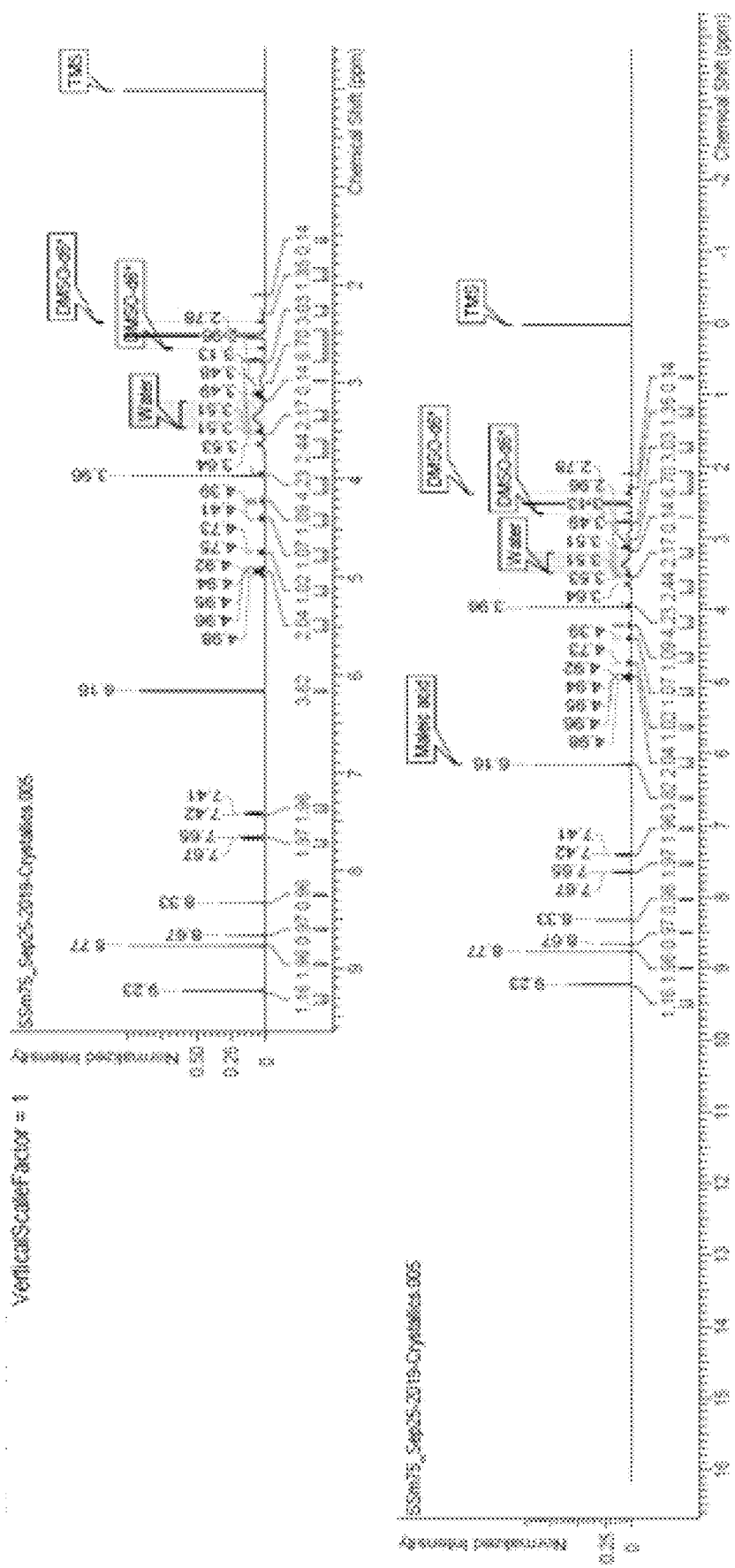
FIG. 3 shows an exemplary result of an H-NMR analysis of the maleate salt of Chemical Formula 1.

Mass loss due to change in humidity is very low as shown in the DVS analysis for the compound of Chemical Formula 2 (FIG. 2) in the relevant humidity range below 80%. The hygroscopicity properties of the maleate salt impart surprisingly improved storage and storage stability compared to the pure material.

The physical and chemical stability study was performed on the compounds of Chemical Formula 2 and Chemical Formula 1 (for reference purposes). The long-term stability study was conducted at defined temperatures and relative humidity levels (25° C./60% relative humidity (RH) and 40° C./75% RH). At regular intervals, a solid sample was analyzed by XRPD, TGMS and HPLC.

The maleate salt was the least hygroscopic solid form since no significant water uptake after incubation for 15 months was recorded under the tested conditions.

Figure 5:
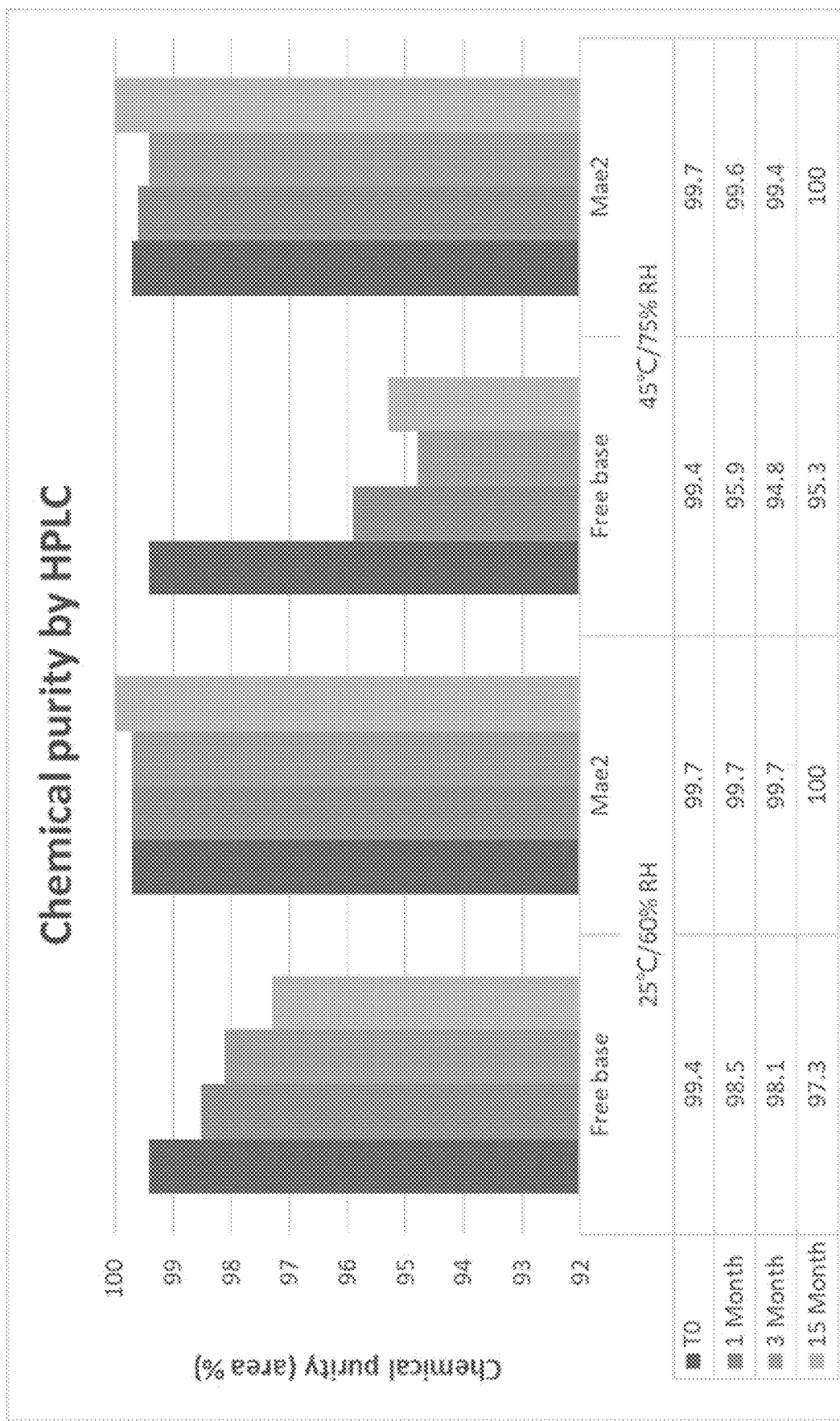
FIG. 5 shows an exemplary result of a chemical purity test by HPLC of the maleate salt described herein.

The results of the chemical purity determination for the compounds of Chemical Formula 1 and Chemical Formula 2 after 1-, 3- and 15-month exposure to 25° C./60% RH and 40° C./75% RH is presented in FIGS. 4 and 5.

Chemical Formula 1 Form A showed partial chemical degradation over time after incubation at 25° C./60% RH and more degradation at 40° C./75% RH. The compound of Chemical Formula 2 did not show significant chemical degradation after exposure to 25° C./60% RH. The compound of Chemical Formula 2 remained chemically stable up to 15 months at 40° C./75% RH.

The exemplary experiments summarized in FIGS. 4 and 5 show that the maleate salt has a chemical purity of at least about 4.7% greater than the free base form represented by Chemical Formula 1 after about 15 months at 40° C. and 75% relative humidity and the maleate salt has a water content of at least about 22% lower than the free base form represented by Chemical Formula 1 after about 15 months at 40° C. and 75% relative humidity.

Based on these results, we can conclude that the compound of Chemical Formula 2 is the least hygroscopic salt and showed improved chemical stability compared to the compound of Chemical Formula 1.

In view of developing a formulation suitable for parenteral administration, the quantitative solubility of Chemical Formula land the Chemical Formula 2 were determined in phosphate buffer pH 7.4, supplemented with solubility-enhancing excipients. The target concentration is 1-1.3 mg/mL.

Based on the qualitative solubility result determined for the PBS formulation vehicle containing Transcutol (Gattefossé, France) and TPGS (tocopherol polyethylene glycol succinate), the quantitative solubility of the compound of Chemical Formula 1 and the compound of Chemical Formula 2 was determined in those vehicles to assess the maximum solubility in those vehicles. The thermodynamic solubility was then determined in PBS buffer containing Transcutol (50% and 10%) and TPGS (20% and 10%) and also in the formulation vehicles containing PEG 400 (50%, with and without presence of 2% DMSO). Suspensions of the compound of Chemical Formula 1 and the compound of Chemical Formula 2 were prepared in the selected vehicles with a compound of Chemical Formula 1 concentration of about 3.5-5 mg/mL. After incubation for 24 hours at room temperature, the solids and liquid phases were separated. The concentration of API in solution was determined by HPLC analysis. The results can be found in FIG. 6.

The compound of Chemical Formula 1 had a solubility of about 1 mg/mL or higher in the formulation vehicles containing 50% Transcutol, 10% TPGS and 20% TPGS. In the vehicles containing PEG 400, the solubility was about 0.3 mg/mL and with only 10% Transcutol the solubility was about 0.1 mg/mL.

The compound of Chemical Formula 2 appeared to have a solubility higher than 1.3 mg/mL in almost all vehicles, except for the vehicle with 10% Transcutol. In the vehicle containing 50% Transcutol, the salt was completely dissolved, and no precipitation occurred after 24 hours, therefore, the solubility was higher than 3.5 mg/mL.

The pH of the solutions recovered from the free base experiments were shifted to higher pH values, while the pH values of the samples with Chemical Formula 2 were shifted to lower pH. The solubility of the compound of Chemical Formula 2 appeared to be higher than that of the compound of Chemical Formula 1 in all the formulation vehicles tested.

From the exemplary results, the maleate salt is more than 75% less soluble than the free base form represented by Chemical Formula 1 at a pH between 1 and 3. In addition, the maleate salt is more than 75% less soluble than the free base form represented by Chemical Formula 1 at a pH of about 1.2 in 0.05M gastric media.

In the present disclosure, there is provided a pharmaceutical composition including the novel salt of a triazolopyrazine derivative represented by Chemical Formula 1 above as active ingredients.

The active ingredient of the pharmaceutical composition used in the present disclosure is a maleate salt of the compound represented by Chemical Formula 2 and an optional pharmaceutically acceptable carrier.

The following exemplary experimental protocol was performed to test the activity of the maleate salt compounds described herein.

An RPMI 1640 cell culture medium, fetal bovine serum (FBS) and trypsin were purchased from GIBCO Co., Ltd. (Grand Island, N.Y.), and sodium hydrogencarbonate, amphotericin B and gentamycin were used as signamic medical products. In addition, reagents such as sulforhodamine (SRB) B, Trisma Base, and trichloroacetic acid (TCA), which were reagents used in a cytotoxicity measurement experiment, were purchased from Sigma Chemical Co., Ltd. For MTS analysis, a Celltiter 96 Aqueous Non-Radioactive Cell Proliferation Assay product was purchased from Promega Co., Ltd. Further, a T-25 culture container used for cell culture, a 96-well plate and other disposable glass used for cell culture were obtained from Folkon (Lincoln Park, N.J.) products.

A drug used in the experiment was diluted as an experimental medium to a desired concentration in the test, and the final dimethylsulfoxide concentration was 0.5% or less.

Cancer cell lines used in the experiment were human-derived cancer cell lines, and a lung cancer cell line EBC-1. RPMI 1640 medium with 10% fetal bovine serum (FBS) was used and cultured in an incubator of 37° C. and 5% $CO_2$ and subcultured once by 3 to 4 days.

Specifically, after the culture with the compound of the present disclosure was terminated, the culture solution was removed, and a cold TCA solution added to each well. The cells were left at 4° C. for 1 hour to be fixed. The TCA solution was removed, and the cells were dried at room temperature, incubated with a solution obtained by dissolving 0.4% SRB in a 1% acetic acid solution, left at room temperature for 30 minutes, and then stained. Extra SRB which was not bound to the cells was washed with a 1% acetic acid solution, and the SRB was eluted by adding a 10 mm tris buffer solution (trisma base; unbuffered) of pH 10.3 to 10.5 to the stained cells.

The results of the cancer cell proliferation inhibitory experiments of the salts were shown in the following Table 6.

TABLE 6

| Cell line | | Chemical Formula 2 | Chemical Formula 1 |
|---|---|---|---|
| Cell activity (GI50) | EBC-1 | 14.17 nM | 8.17 nM |

In one aspect, the novel salt of the triazolopyrazine derivative represented by Chemical Formula 2 provided in the present disclosure had improved activity in inhibiting cancer cell growth compared to the compound of Chemical Formula 1.

What is claimed is:

1. A maleate salt of a triazolopyrazine derivative represented by Chemical Formula 2, wherein the maleate salt has a chemical purity of at least about 4.7% greater than a free base form represented by Chemical Formula 1 after about 15 months at 40 ° C. and 75% relative humidity:

[Chemical Formula 1]

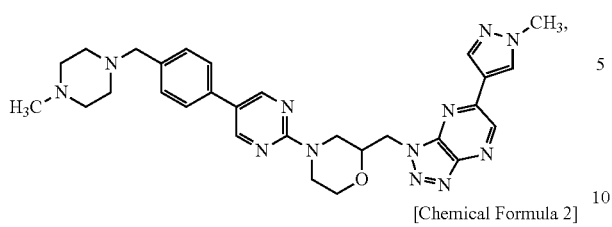

[Chemical Formula 2]

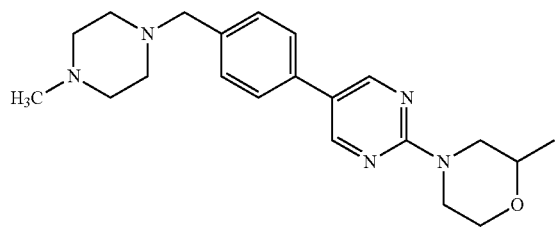

-continued

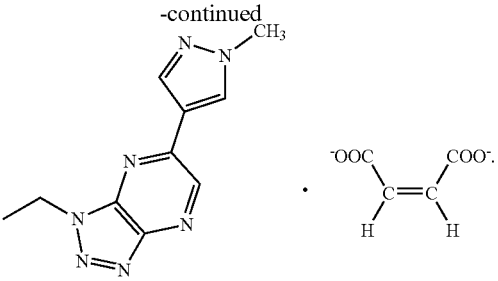

2. A maleate salt of a triazolopyrazine derivative represented by Chemical Formula 2, wherein the maleate salt has a water content of at least about 22% lower than the free base form represented by Chemical Formula 1 after about 15 months at 40 ° C. and 75% relative humidity:

[Chemical Formula 1]

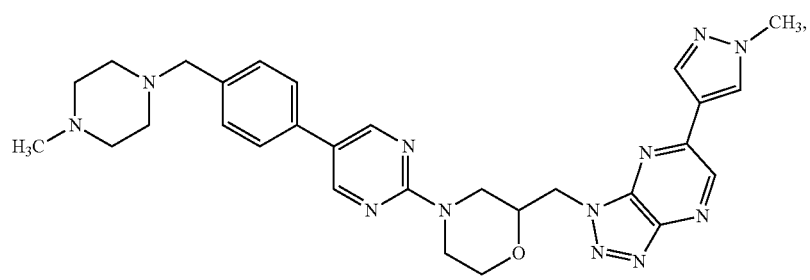

[Chemical Formula 2]

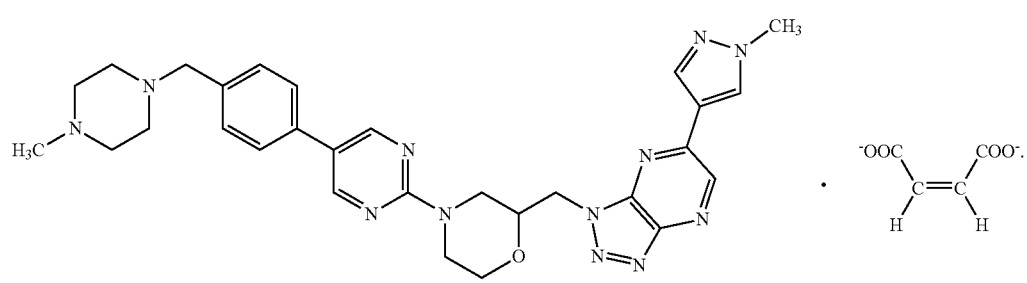

3. A maleate salt of a triazolopyrazine derivative represented by Chemical Formula 2, wherein the maleate salt is more than 75% less soluble than the free base form represented by Chemical Formula 1 at a pH between 1 and 3:

[Chemical Formula 1]

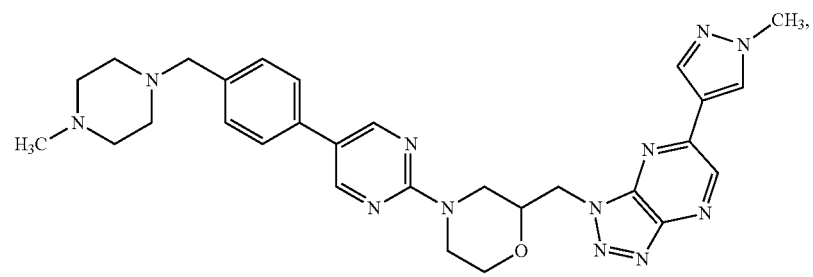

-continued

[Chemical Formula 2]

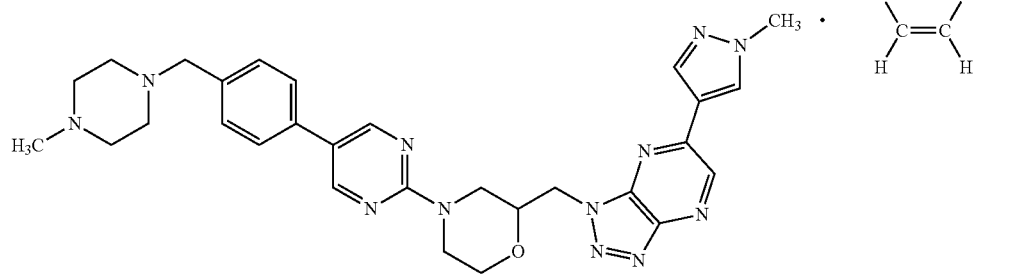

4. A maleate salt of a triazolopyrazine derivative represented by Chemical Formula 2, wherein the maleate salt is more than 75% less soluble than the free base form represented by Chemical Formula 1 at a pH of about 1.2 in 0.05 M gastric media:

[Chemical Formula 1]

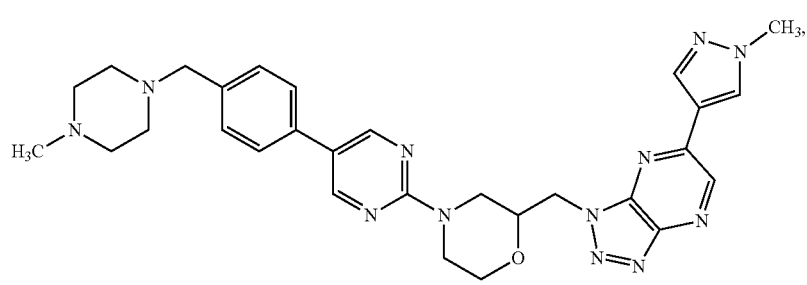

[Chemical Formula 2]

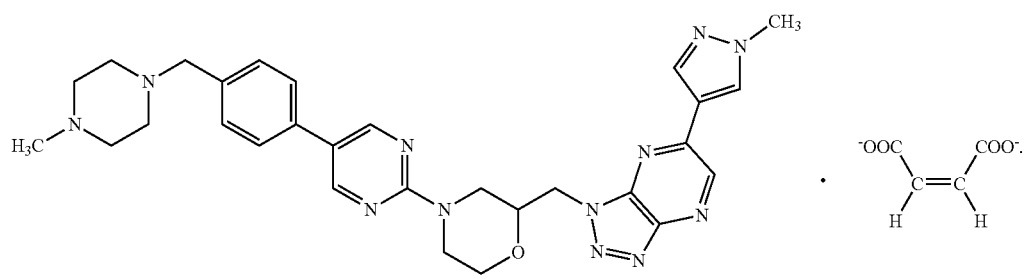

5. A method for manufacturing a maleate salt of a triazolopyrazine derivative, the method comprising:
   (a) adding a compound represented by Chemical Formula 1 below to a reactor containing a solvent;

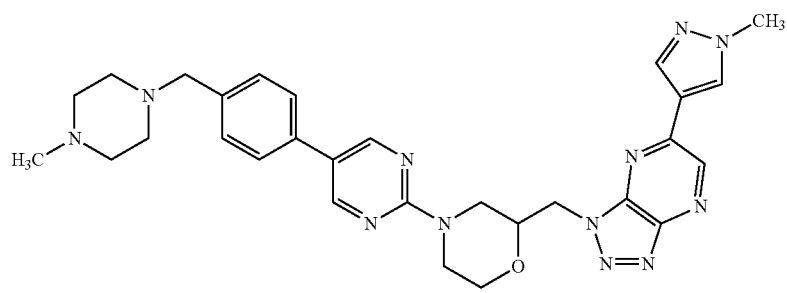

(b) stirring the compound and the solvent in the reactor to form a first solution;
(c) adding maleic acid to the first solution in an equivalent ratio of about 1:1 to about 1:3 with respect to Chemical Formula 1 to form a second solution;
(d) stirring the maleic acid in the second solution to form a third solution; and
(e) cooling the third solution to obtain a precipitate of the maleate salt represented by Chemical Formula 2:

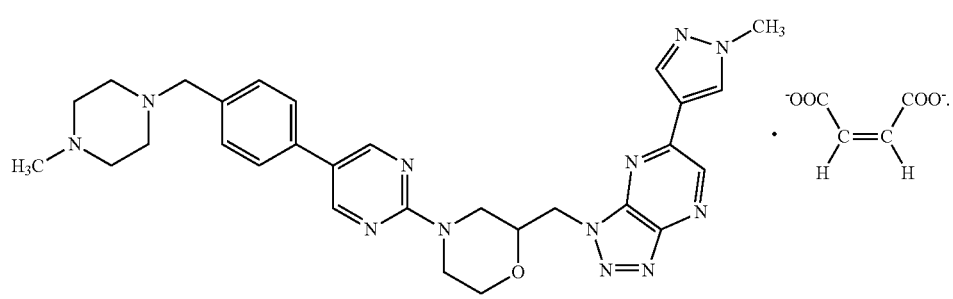

[Chemical Formula 2]

6. The method of claim 5, wherein the maleate salt comprises at least one maleic acid molecule.
7. The method of claim 6, wherein the maleate salt comprises at least two maleic acid molecules.
8. The method of claim 5, wherein the solvent is selected from the group consisting of acetonitrile, acetone, and 1,2-dimethoxyethane.
9. The method of claim 5, wherein step (b) is performed at about 50° C. for at least about 1 hour.
10. The method of claim 5, wherein the precipitate is cooled to about 25° C. and then aged for at least about 24 to 48 hours.
11. A pharmaceutical composition comprising a maleate salt of a triazolopyrazine derivative, represented by Chemical Formula 2 below and a pharmaceutically acceptable carrier

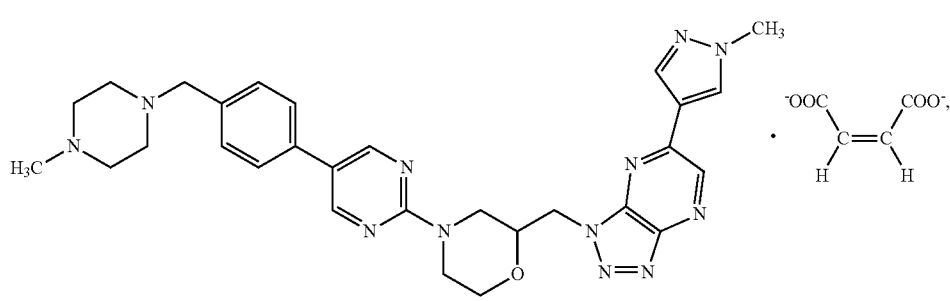

[Chemical Formula 2]

wherein the malate salt has a chemical purity of at least about 4.7% greater than a free base form represented by Chemical Formula 1 after about 15 months at 40° C. and 75% relative humidity

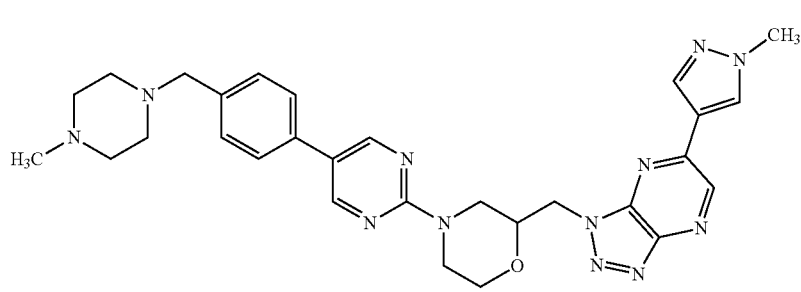

[Chemical Formula 1]

12. The pharmaceutical composition of claim 11, wherein the pharmaceutically acceptable carrier is selected from the group consisting of one or more of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil.

13. The pharmaceutical composition of claim 11, further comprising one or more of a lubricant, a wetting agent, a sweetening agent, a flavoring agent, an emulsifying agent, a suspending agent, and a preservative.

14. A method of inhibiting the activity of c-Met kinase in a subject comprising administering a maleate salt of a triazolopyrazine derivative, represented by Chemical Formula 2 to a subject in need of treatment for a disorder associated with an increased activity of c-Met kinase:

[Chemical Formula 2]

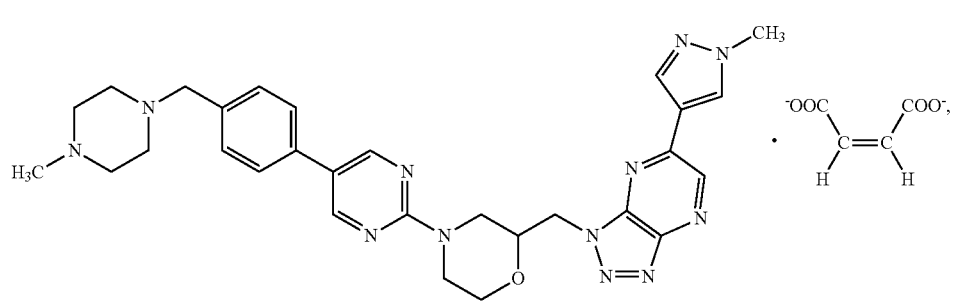

wherein the malate salt has a chemical purity of at least about 4.7% greater than a free base form represented by Chemical Formula 1 after about 15 months at 40° C. and 75% relative humidity

[Chemical Formula 1]

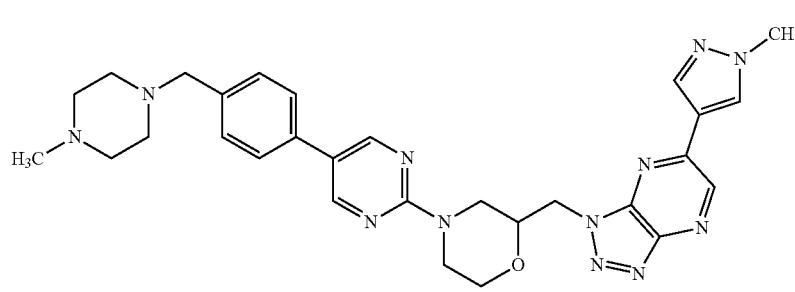

15. The method of claim 14, wherein the disorder is a hyperproliferative disorder.

16. The method of claim 15, wherein the hyperproliferative disorder is selected from the group consisting of lung cancer, gastric cancer, pancreatic cancer, colon cancer, ovarian cancer, renal cell cancer, prostate cancer and a brain tumor.

17. The method of claim 14, wherein the maleate salt is administered in a therapeutically effective amount to the subject.

18. A pharmaceutical composition comprising a maleate salt of a triazolopyrazine derivative, represented by Chemical Formula 2 below and a pharmaceutically acceptable carrier

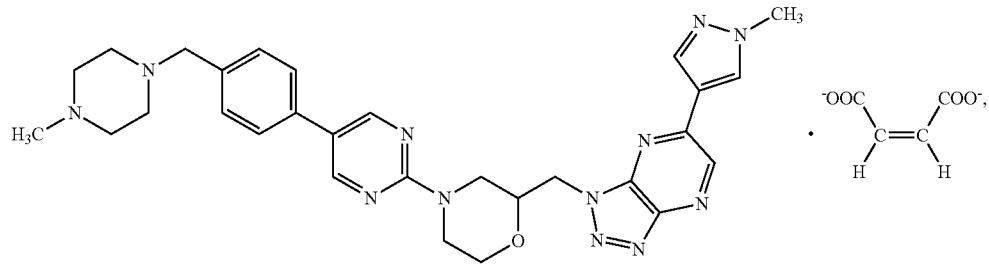

[Chemical Formula 2]

wherein the maleate salt has a water content of at least about 22% lower than the free base form represented by Chemical Formula 1 after about 15 months at 40° C. and 75% relative humidity:

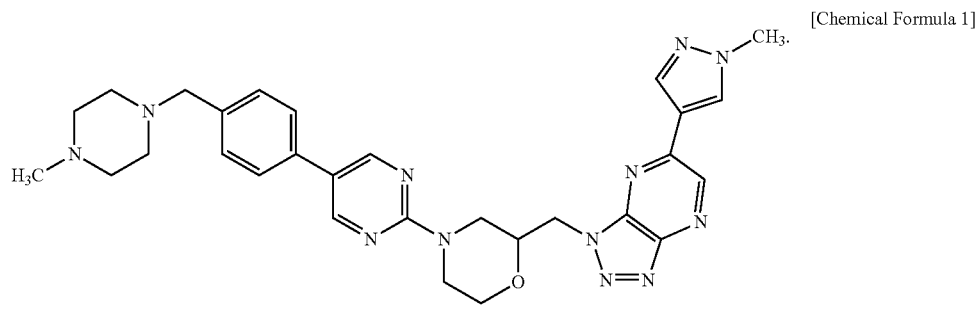 [SMILES: CN1CCN(Cc2ccc(-c3cnc(N4CCOC(Cn5nnc6ncc(-c7cnn(C)c7)nc65)C4)nc3)cc2)CC1]

[Chemical Formula 1]

19. The pharmaceutical composition of claim 18, wherein the pharmaceutically acceptable carrier is selected from the group consisting of one or more of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil.

20. The pharmaceutical composition of claim 18, further comprising one or more of a lubricant, a wetting agent, a sweetening agent, a flavoring agent, an emulsifying agent, a suspending agent, and a preservative.

21. A method of inhibiting the activity of c-Met kinase in a subject comprising administering a maleate salt of a triazolopyrazine derivative, represented by Chemical Formula 2 to a subject in need of treatment for a disorder associated with an increased activity of c-Met kinase:

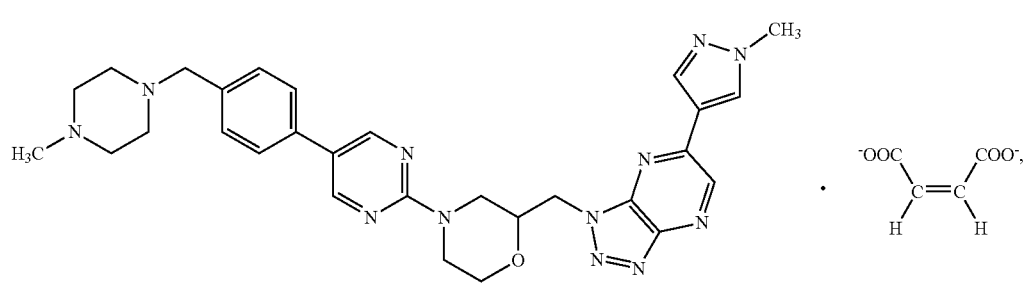

[Chemical Formula 2]

wherein the maleate salt has a water content of at least about 22% lower than the free base form represented by Chemical Formula 1 after about 15 months at 40° C. and 75% relative humidity:

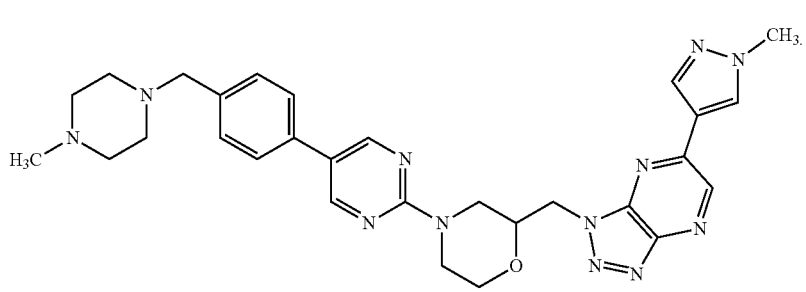

[Chemical Formula 1]

22. The method of claim 21, wherein the disorder is a hyperproliferative disorder.

23. The method of claim 22, wherein the hyperproliferative disorder is selected from the group consisting of lung cancer, gastric cancer, pancreatic cancer, colon cancer, ovarian cancer, renal cell cancer, prostate cancer and a brain tumor.

24. The method of claim 21, wherein the maleate salt is administered in a therapeutically effective amount to the subject.

25. A pharmaceutical composition comprising a maleate salt of a triazolopyrazine derivative, represented by Chemical Formula 2 below and a pharmaceutically acceptable carrier:

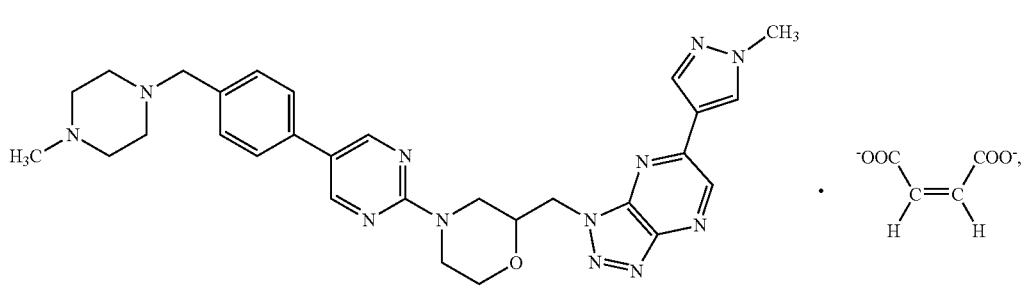

[Chemical Formula 2]

wherein the maleate salt is more than 75% less soluble than the free base form represented by Chemical Formula 1 at a pH between 1 and 3:

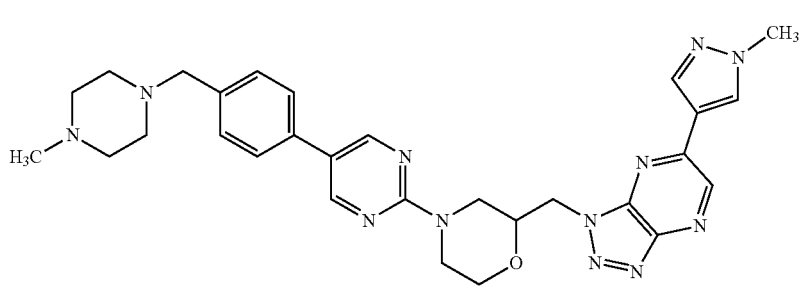

[Chemical Formula 1]

26. The pharmaceutical composition of claim 25, wherein the pharmaceutically acceptable carrier is selected from the group consisting of one or more of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil.

27. The pharmaceutical composition of claim 25, further comprising one or more of a lubricant, a wetting agent, a sweetening agent, a flavoring agent, an emulsifying agent, a suspending agent, and a preservative.

28. A method of inhibiting the activity of c-Met kinase in a subject comprising administering a maleate salt of a triazolopyrazine derivative, represented by Chemical Formula 2 to a subject in need of treatment for a disorder associated with an increased activity of c-Met kinase:

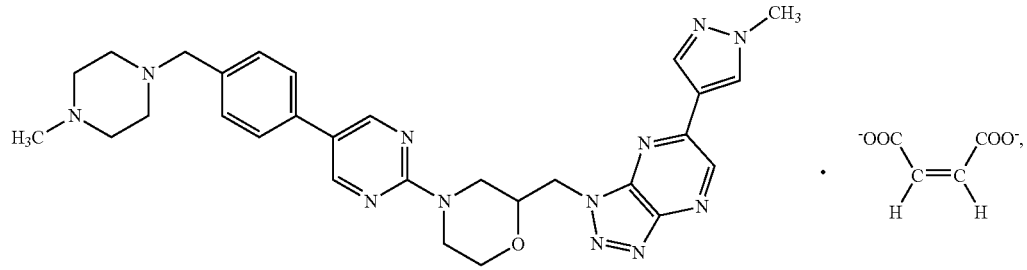

[Chemical Formula 2]

wherein the maleate salt is more than 75% less soluble than the free base form represented by Chemical Formula 1 at a pH between 1 and 3:

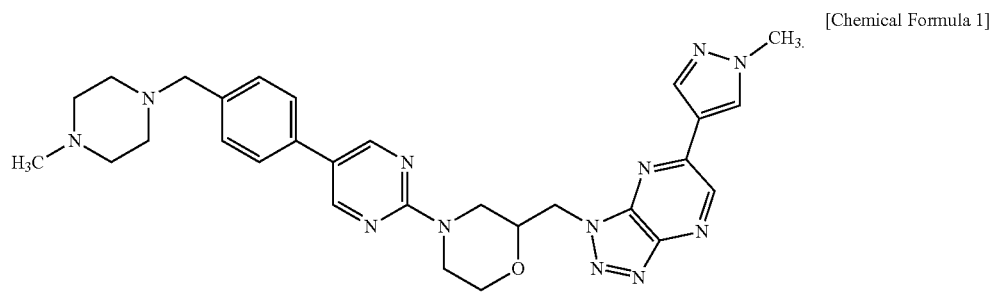 [SMILES: CN1CCN(Cc2ccc(-c3cnc(N4CCOC(Cn5nnc6ncc(-c7cnn(C)c7)nc65)C4)nc3)cc2)CC1]

[Chemical Formula 1]

29. The method of claim 28, wherein the disorder is a hyperproliferative disorder.

30. The method of claim 29, wherein the hyperproliferative disorder is selected from the group consisting of lung cancer, gastric cancer, pancreatic cancer, colon cancer, ovarian cancer, renal cell cancer, prostate cancer and a brain tumor.

31. The method of claim 28, wherein the maleate salt is administered in a therapeutically effective amount to the subject.

32. A pharmaceutical composition comprising a maleate salt of a triazolopyrazine derivative, represented by Chemical Formula 2 below and a pharmaceutically acceptable carrier

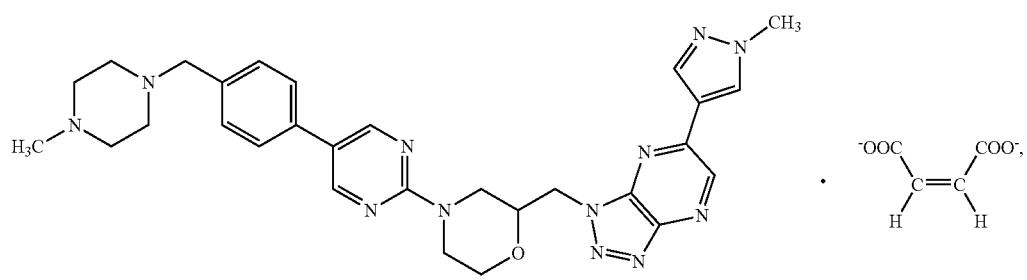

[Chemical Formula 2]

wherein the maleate salt is more than 75% less soluble than the free base form represented by Chemical Formula 1 at a pH of about 1.2 in 0.05M gastric media:

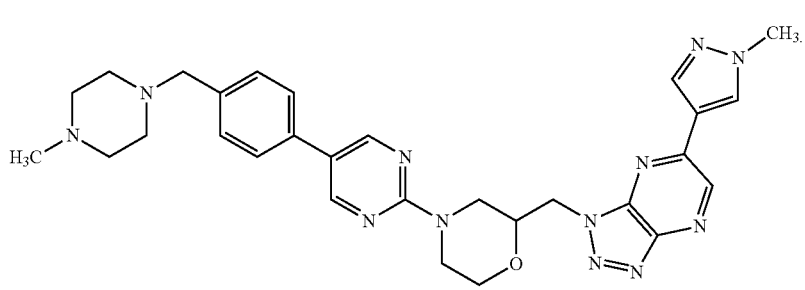

[Chemical Formula 1]

33. The pharmaceutical composition of claim 32, wherein the pharmaceutically acceptable carrier is selected from the group consisting of one or more of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil.

34. The pharmaceutical composition of claim 32, further comprising one or more of a lubricant, a wetting agent, a sweetening agent, a flavoring agent, an emulsifying agent, a suspending agent, and a preservative.

35. A method of inhibiting the activity of c-Met kinase in a subject comprising administering a maleate salt of a triazolopyrazine derivative, represented by Chemical Formula 2 to a subject in need of treatment for a disorder associated with an increased activity of c-Met kinase:

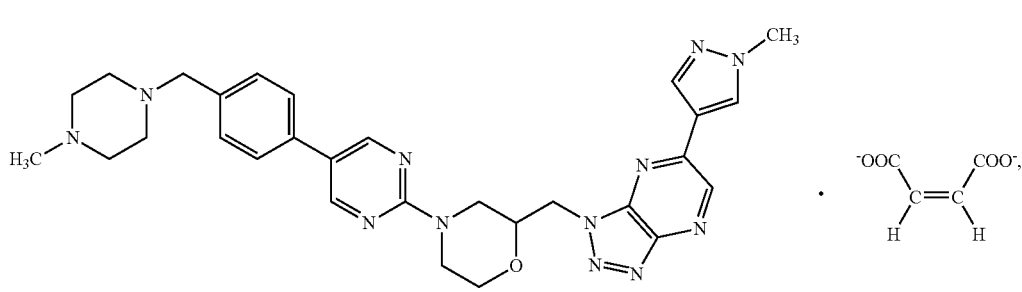

[Chemical Formula 2]

wherein the maleate salt is more than 75% less soluble than the free base form represented by Chemical Formula 1 at a pH of about 1.2 in 0.05 M gastric media:

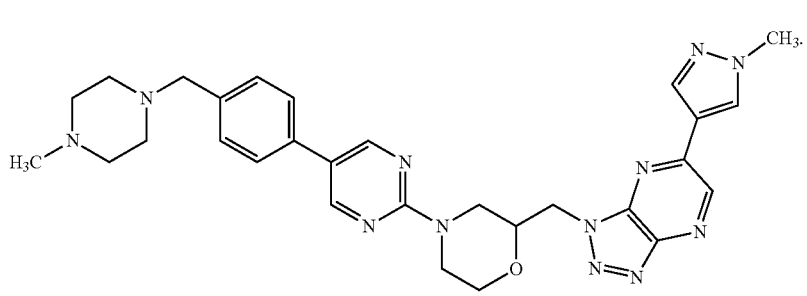

[Chemical Formula 1]

36. The method of claim 35, wherein the disorder is a hyperproliferative disorder.

37. The method of claim 36, wherein the hyperproliferative disorder is selected from the group consisting of lung cancer, gastric cancer, pancreatic cancer, colon cancer, ovarian cancer, renal cell cancer, prostate cancer and a brain tumor.

38. The method of claim 35, wherein the maleate salt is administered in a therapeutically effective amount to the subject.

* * * * *